US012636234B2

(12) United States Patent
Yamaguchi et al.

(10) Patent No.: US 12,636,234 B2

(45) Date of Patent: May 26, 2026

(54) METHOD OF PRODUCING POLYURETHANE-BASED COMPOSITE MATERIAL, POLYURETHANE-BASED COMPOSITE MATERIAL, AND MATERIAL FOR DENTAL CUTTING WORK

(71) Applicant: TOKUYAMA DENTAL CORPORATION, Tokyo (JP)

(72) Inventors: Takamasa Yamaguchi, Tokyo (JP); Takuya Suzuki, Tokyo (JP)

(73) Assignee: TOKUYAMA DENTAL CORPORATION (JP)

( * ) Notice: Subject to any disclaimer, the term of this patent is extended or adjusted under 35 U.S.C. 154(b) by 494 days.

(21) Appl. No.: 17/791,778

(22) PCT Filed: Jan. 22, 2021

(86) PCT No.: PCT/JP2021/002205

§ 371 (c)(1),
(2) Date: Jul. 8, 2022

(87) PCT Pub. No.: WO2021/153446

PCT Pub. Date: Aug. 5, 2021

(65) Prior Publication Data

US 2023/0088142 A1 Mar. 23, 2023

(30) Foreign Application Priority Data

Jan. 28, 2020 (JP) ................................ 2020-011354

(51) Int. Cl.

| | |
|---|---|
| ***A61K 6/893*** | (2020.01) |
| ***C08F 290/14*** | (2006.01) |
| ***C08K 3/22*** | (2006.01) |
| ***C08K 3/36*** | (2006.01) |
| ***C08K 5/5419*** | (2006.01) |
| ***C08K 9/06*** | (2006.01) |

(52) U.S. Cl.

CPC .......... *A61K 6/893* (2020.01); *C08F 290/147* (2013.01); *C08K 3/22* (2013.01); *C08K 3/36* (2013.01); *C08K 5/5419* (2013.01); *C08K 9/06* (2013.01); *C08K 2003/2241* (2013.01); *C08K 2003/2244* (2013.01)

(58) Field of Classification Search

CPC ....... A61K 6/893; C08F 290/147; C08K 3/22; C08K 3/36; C08K 5/5419; C08K 9/06; C08K 2003/2241; C08K 2003/2244

See application file for complete search history.

(56) References Cited

U.S. PATENT DOCUMENTS

| | | | |
|---|---|---|---|
| 4,787,850 A | 11/1988 | Michl et al. | |
| 6,818,725 B2 | 11/2004 | Klare et al. | |
| 7,132,459 B1 | 11/2006 | Buchel | |
| 8,114,920 B2 | 2/2012 | Kim et al. | |
| 2002/0090525 A1* | 7/2002 | Rusin | A61K 6/887 428/542.8 |
| 2003/0008967 A1* | 1/2003 | Hecht | C08G 18/6245 106/35 |
| 2003/0083400 A1* | 5/2003 | Jia | A61K 6/889 523/115 |
| 2003/0166741 A1 | 9/2003 | Klare et al. | |
| 2009/0012201 A1 | 1/2009 | Kim et al. | |
| 2012/0010357 A1* | 1/2012 | Bruchmann | C08G 83/005 528/73 |
| 2016/0136059 A1* | 5/2016 | Hecht | A61K 6/893 523/115 |
| 2017/0181932 A1 | 6/2017 | Yoshinaga et al. | |
| 2019/0021815 A1* | 1/2019 | Herrmann | A61C 13/087 |
| 2021/0186820 A1* | 6/2021 | Chakraborty | A61C 7/002 |

FOREIGN PATENT DOCUMENTS

| | | |
|---|---|---|
| CN | 1327456 A | 12/2001 |
| CN | 103974986 A | 8/2014 |
| CN | 106132383 A | 11/2016 |

(Continued)

OTHER PUBLICATIONS

American Chemistry Council, Safety and Handling of Organic Peroxides, Oct. 2023, p. 1-29 (Year: 2023).*
EP0262488A1 machine translation (Year: 1988).*
JP2012072327A machine translation (Year: 2012).*
International Search Report (English and Japanese) issued in PCT/JP2021/002205, mailed Mar. 16, 2021; ISA/JP (5 pages).
Notice of Reasons for Refusal for JP Patent Application No. 2021-573990 (with English translation), dated Apr. 4, 2023 (6 pages).

(Continued)

*Primary Examiner* — Mark Eashoo
*Assistant Examiner* — Caitlin Norine Illing
(74) *Attorney, Agent, or Firm* — Harness, Dickey & Pierce, P.L.C.

(57) ABSTRACT

A method of producing a polyurethane-based composite material includes a step of performing a polyaddition reaction in a first composition containing a radically polymerizable monomer (B) free from causing a polyaddition reaction with any of a radically polymerizable diol compound (a1) and a diisocyanate compound (a2), to thereby form a polyurethane component (A) having a number average molecular weight of from 1,500 to 5,000, a step of preparing a second composition containing the component A, the component B, a radical polymerization initiator, and a filler, and a step of performing radical polymerization using the second composition. A ratio R represented by the following Equation 1 is from 20 mass % to 80 mass %. Equation 1 is R=100×B/[a1+a2+A+B], where a1, a2, A, and B represent the contents (parts by mass) of the components a1, a2, A, and B in the second composition.

6 Claims, No Drawings

(56) References Cited

FOREIGN PATENT DOCUMENTS

| | | | | |
|---|---|---|---|---|
| CN | 108383974 | A | | 8/2018 |
| DE | 0262488 | A1 | * | 4/1988 |
| JP | H11-279236 | A | | 10/1999 |
| JP | 2002-527588 | A | | 8/2002 |
| JP | 2003-261410 | A | | 9/2003 |
| JP | 2008-189808 | A | | 8/2008 |
| JP | 2009-523188 | A | | 6/2009 |
| JP | 2012-036275 | A | | 2/2012 |
| JP | 2012072327 | A | * | 4/2012 |
| JP | 2017-039665 | A | | 2/2017 |
| JP | 2019-210233 | A | | 12/2019 |
| WO | 2016/159294 | A1 | | 10/2016 |

OTHER PUBLICATIONS

Shao-Ming Fang, et al. "Preparation and Characterization of a Series of Novel EuIIII-Complex-Polyurethane Acrylate Materials Based on Mixed 6-Hydroxy-1-naphthoate and 1,10-Phenanthroline Ligands"; Journal of Applied Polymer Science; col. 125, No. 5; published online on Feb. 3, 2012 in Wiley Online Library (wileyonlinelibrary.com); pp. 3404-3409 (total 6 pages).

"Synthesize and Properties of Multifunctional UV Curing Resin" (English abstract on p. 6); China Outstanding Master's Degree Thesis; Database Engineering Scinece and Technology I series, No. 05; Author unknown; dated Dec. 28, 2006 (totla 86 pages).

Office Action issued in the corresponding Chinese Patent Application No. 202180007558.0; issued on Feb. 18, 2024 (total 13 pages).

* cited by examiner

METHOD OF PRODUCING POLYURETHANE-BASED COMPOSITE MATERIAL, POLYURETHANE-BASED COMPOSITE MATERIAL, AND MATERIAL FOR DENTAL CUTTING WORK

CROSS REFERENCE TO RELATED APPLICATIONS

This application is a U.S. National Phase Application under 35 U.S.C. 371 of International Application No. PCT/JP2021/002205, filed on Jan. 22, 2021, which claims priority to Japanese Patent Application No. 2020-011354, filed on Jan. 28, 2020. The entire disclosures of the above applications are expressly incorporated by reference herein.

BACKGROUND

Technical Field

The present invention relates to a method of producing a polyurethane-based composite material, a polyurethane-based composite material, and a material for dental cutting work.

Background Art

In dental treatment, as one technique for producing a dental prosthesis, such as an inlay, an onlay, a crown, a bridge, or an implant superstructure, there is known a method involving performing cutting work through use of a dental CAD/CAM system. The "dental CAD/CAM system" is a system involving designing a dental prosthesis on the basis of three-dimensional coordinate data through utilization of a computer, and producing a crown restoration through use of a cutting machine or the like. As a material for cutting work, there are used various materials, such as glass ceramics, zirconia, titanium, and a resin. As a resin-based material for dental cutting work, there is used a cured product obtained by using a curable composition containing an inorganic filler such as silica, a polymerizable monomer such as a methacrylate, a polymerization initiator, and the like, and curing the composition into a block shape or a disc shape. The material for cutting work is drawing increasing attention from the viewpoint of: high workability resulting from a smaller number of steps through good use of a computer system than a conventional method of producing a dental prosthesis; or aesthetics of a cured body or strength thereof.

Such material for cutting work is mainly applied at a crown portion, and is required to have higher strength when used as a molar crown or bridge. However, the current material for cutting work is based on a (meth)acrylic resin, and has a problem in that its strength is limited.

On the other hand, a polyurethane resin is known to generally have high strength, and is being considered for use as a dental material. For example, in U.S. Pat. No. 4,787,850 A, there are proposals of a polyurethane-based resin for a dental material application and a method of producing the same. The production method includes a two stage process for producing artificial teeth or crowns, inlays or other tooth parts using a curable dental material. In this method, the first stage includes a process involving: producing a rubbery elastic blank by hardening at ambient temperature a composition containing (A) at least one kind of polyfunctional isocyanate compound, (B) at least one kind of polyol compound, (C) at least one kind of methacrylate monomer having at least two hydroxyl groups, (D) a catalyst for initiating polymerization of the methacrylate monomer with heat or light, and (E) a catalyst for accelerating the formation of a polyurethane from the (A), (B), and (C), which does not catalyze the radical polymerization of the (C); and shaping and mechanically finishing the blank. In addition, the second stage includes a process of curing the shaped rubbery elastic blank to provide the hard artificial teeth or artificial teeth parts.

When the two stage process described above is utilized, the blank obtained by filling an inside of a cavity of a tooth with the composition and performing the hardening in the first stage has elasticity, and hence a dentist can easily remove the blank from the cavity and can perform the curing in the second stage on the spot through, for example, photoirradiation thereafter. Accordingly, the above-mentioned two stage process is suitable for producing a temporary crown and bridge for provisional filling (a temporary crown and bridge material).

In addition, also in JP 2002-527588 A, there is a disclosure of a technology of a two stage process involving forming a preform through utilization of a polyaddition reaction, and then curing the preform into a high-strength molded body through radical polymerization. Besides, in JP 2002-527588 A, there is also a disclosure that the molded body (molded body based on a polyurethane material) can be utilized in extremely diverse applications.

Further, in JP 2019-210233 A, there is a proposal of a dental restoration material formed of a polyurethane resin satisfying the following conditions I and II or a composite material using the polyurethane resin:

$$BS_A \geq 200 \text{ (MPa)} \qquad \text{Condition I:}$$

$$1 > BS_W/BS_A \geq 0.7 \qquad \text{Condition II:}$$

where $BS_A$ represents a three-point bending strength (MPa) according to ISO 6872, and $BS_W$ represents a three-point bending strength (MPa) after immersion in water according to JDMAS 245:2017.

In this connection, when a resin material for dental cutting work formed of the above-mentioned dental restoration material is produced, the following method is utilized: a polymerizable composition serving as a raw material is cast and then heated, and is polymerized and cured through urethane bond formation and radical polymerization during the heating.

As described in JP 2019-210233 A, the material obtained by the method described in U.S. Pat. No. 4,787,850 A or JP 2002-527588 A uses a polyurethane resin as a main component. Accordingly, the material is conceived to be excellent in strength, but depending on the kind of the polyurethane and the degree of progress of its reaction, the radical polymerization of the second stage may fail to sufficiently progress, leading to an adverse influence on strength, particularly water resistance. On the other hand, the composite material disclosed in JP 2019-210233 A has high strength, and also has water resistance for maintaining high strength even under a wet environment such as in water.

However, when the inventors of the present invention followed the method of producing the composite material described in JP 2019-210233 A to produce the composite material, it was found that the uniformity of the resultant cured body was insufficient in some cases.

The present invention has been made in view of the above-mentioned circumstances, and an object of the present invention is to provide a method of producing a polyurethane-based composite material by which a cured body excellent not only in strength and water resistance but also in uniformity can be easily produced, and a polyurethane-based composite material and a material for dental cutting work each of which is produced using the method of producing a polyurethane-based composite material, and is also excellent in bonding properties.

SUMMARY

The above-mentioned object is achieved by the present invention to be described below.

That is, according to one embodiment of the present invention, there is provided a method of producing a polyurethane-based composite material, including: a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), to thereby form a polyurethane component (A) having a number average molecular weight of from 1,500 to 5,000 and having a radically polymerizable group; a radically polymerizable raw material composition-preparing step of preparing a radically polymerizable raw material composition containing the polyurethane component (A), the polymerizable monomer (B), a radical polymerization initiator (C), and a filler (D); and a radical polymerization step of performing radical polymerization using the radically polymerizable raw material composition after completion of the polyaddition reaction step and the radically polymerizable raw material composition-preparing step, to thereby form a polyurethane-based composite material, wherein a polymerizable monomer blending ratio Rr represented by the following equation (1) is from 20 mass % to 80 mass %:

$$Rr=100\times Br/[a1r+a2r+Ar+Br] \qquad \text{Equation (1)}$$

in the equation (1), a1r represents a content (parts by mass) of the diol compound (a1) remaining unreacted in the radically polymerizable raw material composition, a2r represents a content (parts by mass) of the diisocyanate compound (a2) remaining unreacted in the radically polymerizable raw material composition, Ar represents a content (parts by mass) of the polyurethane component (A) in the radically polymerizable raw material composition, and Br represents a content (parts by mass) of the polymerizable monomer (B) in the radically polymerizable raw material composition.

In the method of producing a polyurethane-based composite material according to the one embodiment of the present invention, it is preferred that a content ratio of the filler (D) in the radically polymerizable raw material composition be from 60 mass % to 85 mass %.

In the method of producing a polyurethane-based composite material according to the one embodiment of the present invention, it is preferred that the polymerizable monomer (B) contain a polymerizable monomer represented by the following structural formula (1):

(1)

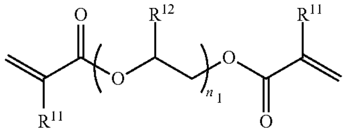

in the structural formula (1), $R^{11}$ and $R^{12}$ each represent a hydrogen atom or a methyl group, and $n_1$ represents an integer of from 1 to 10.

In the method of producing a polyurethane-based composite material according to the one embodiment of the present invention, it is preferred that the diol compound (a1) be a diol compound in which a number of constituent atoms of a main chain in a divalent organic residue interposed between two hydroxyl groups contained in the diol compound is from 2 to 8.

In the method of producing a polyurethane-based composite material according to the one embodiment of the present invention, it is preferred that the radical polymerization initiator (C) to be used be a thermal radical polymerization initiator, and the radical polymerization step be carried out under heating at a temperature that is from −10° C. to +25° C. with respect to a 10-hour half-life temperature of the thermal radical polymerization initiator.

In the method of producing a polyurethane-based composite material according to the one embodiment of the present invention, it is preferred that the polyaddition-reactive raw material composition be prepared by: preparing a primary raw material composition containing the diol compound (a1), the polymerizable monomer (B), and the filler (D); and further adding the diisocyanate compound (a2) to the primary raw material composition.

In the method of producing a polyurethane-based composite material according to the one embodiment of the present invention, it is preferred that the radically polymerizable raw material composition be a paste-like composition.

In the method of producing a polyurethane-based composite material according to the one embodiment of the present invention, it is preferred that the radical polymerization step be carried out after the radically polymerizable raw material composition is poured into a mold.

According to a first aspect of the present invention, there is provided a polyurethane-based composite material, which is produced through: a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), to thereby form a polyurethane component (A) having a number average molecular weight of from 1,500 to 5,000 and having a radically polymerizable group; a radically polymerizable raw material composition-preparing step of preparing a radically polymerizable raw material composition containing the polyurethane component (A), the polymerizable monomer (B), a radical polymerization initiator (C), and a filler (D); and a radical polymerization step of performing radical polymerization using the radically polymerizable raw material composition after completion of the polyaddition reaction step and the radically polymerizable raw material composition-preparing step, to thereby form the polyurethane-based composite material, wherein a polymerizable monomer blending ratio Rr represented by the following equation (1) is from 20 mass % to 80 mass %, wherein a content ratio of the filler (D) in the radically polymerizable raw material composition is from 60 mass % to 85 mass %, wherein the radical polymerization initiator (C) to be used is a thermal radical polymerization initiator, wherein the radical polymerization step is carried out under heating at a temperature that is from −10° C. to +25° C. with respect to a 10-hour half-life temperature of the thermal radical polymerization initiator, and wherein 10% to 25% of a total amount of the radically polymerizable groups of the diol compound (a1) and the polymerizable monomer (B) that are contained in the radically polymerizable raw material composition remains in a copolymer of the polyurethane component (A) and the polymerizable monomer (B), the copolymer being formed in the radical polymerization step:

$$Rr=100\times Br/[a1r+a2r+Ar+Br] \quad \text{Equation (1)}$$

in the equation (1), a1r represents a content (parts by mass) of the diol compound (a1) remaining unreacted in the radically polymerizable raw material composition, a2r represents a content (parts by mass) of the diisocyanate compound (a2) remaining unreacted in the radically polymerizable raw material composition, Ar represents a content (parts by mass) of the polyurethane component (A) in the radically polymerizable raw material composition, and Br represents a content (parts by mass) of the polymerizable monomer (B) in the radically polymerizable raw material composition.

According to a second aspect of the present invention, there is provided a polyurethane-based composite material, including a composite material containing: a polyurethane-based resin matrix; and a filler dispersed and incorporated in the polyurethane-based resin matrix, wherein the polyurethane-based resin matrix is formed of a copolymer of: a polyurethane having a number average molecular weight of from 1,500 to 5,000 and having a radically polymerizable group; and a radically polymerizable monomer free from causing a polyaddition reaction with a hydroxyl group and an isocyanate group, wherein a content of radically polymerizable carbon-carbon double bonds per g of the polyurethane-based resin matrix is from 0.5 mmol/g to 1.0 mmol/g, and wherein a content of the filler in the composite material is from 60 mass % to 85 mass %.

According to a first aspect of the present invention, there is provided a material for dental cutting work, including a polyurethane-based composite material, which is produced through: a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), to thereby form a polyurethane component (A) having a number average molecular weight of from 1,500 to 5,000 and having a radically polymerizable group; a radically polymerizable raw material composition-preparing step of preparing a radically polymerizable raw material composition containing the polyurethane component (A), the polymerizable monomer (B), a radical polymerization initiator (C), and a filler (D); and a radical polymerization step of performing radical polymerization using the radically polymerizable raw material composition after completion of the polyaddition reaction step and the radically polymerizable raw material composition-preparing step, to thereby form the polyurethane-based composite material, wherein a polymerizable monomer blending ratio Rr represented by the following equation (1) is from 20 mass % to 80 mass %, wherein a content ratio of the filler (D) in the radically polymerizable raw material composition is from 60 mass % to 85 mass %, wherein the radical polymerization initiator (C) to be used is a thermal radical polymerization initiator, wherein the radical polymerization step is carried out under heating at a temperature that is from −10° C. to +25° C. with respect to a 10-hour half-life temperature of the thermal radical polymerization initiator, and wherein 10% to 25% of a total amount of the radically polymerizable groups of the diol compound (a1) and the polymerizable monomer (B) that are contained in the radically polymerizable raw material composition remains in a copolymer of the polyurethane component (A) and the polymerizable monomer (B), the copolymer being formed in the radical polymerization step:

$$Rr=100\times Br/[a1r+a2r+Ar+Br] \quad \text{Equation (1)}$$

in the equation (1), a1r represents a content (parts by mass) of the diol compound (a1) remaining unreacted in the radically polymerizable raw material composition, a2r represents a content (parts by mass) of the diisocyanate compound (a2) remaining unreacted in the radically polymerizable raw material composition, Ar represents a content (parts by mass) of the polyurethane component (A) in the radically polymerizable raw material composition, and Br represents a content (parts by mass) of the polymerizable monomer (B) in the radically polymerizable raw material composition.

According to a second aspect of the present invention, there is provided a material for dental cutting work, including a polyurethane-based composite material, including a composite material containing: a polyurethane-based resin matrix; and a filler dispersed and incorporated in the polyurethane-based resin matrix, wherein the polyurethane-based resin matrix is formed of a copolymer of: a polyurethane having a number average molecular weight of from 1,500 to 5,000 and having a radically polymerizable group; and a radically polymerizable monomer free from causing a polyaddition reaction with a hydroxyl group and an isocyanate group, wherein a content of radically polymerizable carbon-carbon double bonds per g of the polyurethane-based resin matrix is from 0.5 mmol/g to 1.0 mmol/g, and wherein a content of the filler in the composite material is from 60 mass % to 85 mass %.

Advantageous Effects of Invention

As described above, according to the present invention, the method of producing a polyurethane-based composite material by which a cured body excellent not only in strength and water resistance but also in uniformity can be easily produced, and the polyurethane-based composite material and the material for dental cutting work each of which is produced using the method of producing a polyurethane-based composite material, and is also excellent in bonding properties can be provided.

DETAILED DESCRIPTION

A method of producing a polyurethane-based composite material according to an embodiment of the present invention, a polyurethane-based composite material according to an embodiment of the present invention, and a material for dental cutting work according to an embodiment of the present invention are described below. In the description of the present application, the expression "from x to y" using numerical values "x" and "y" means "x or more and y or less" unless otherwise stated. When only the numerical value "y" has a unit attached thereto in such expression, the unit also applies to the numerical value "x". In addition, in the description of the present application, the term "(meth) acryl" means both of "acryl" and "methacryl".

1. Method of Producing Polyurethane-Based Composite Material

A method of producing a polyurethane-based composite material according to this embodiment includes: a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), to thereby form a polyurethane component (A) having a number average molecular weight of from 1,500 to 5,000 and having a radically polymerizable group; a radically polymerizable raw material composition-preparing step of preparing a radically polymerizable raw material composition containing the polyurethane component (A), the polymerizable monomer (B), a radical polymerization initiator (C), and a filler (D); and a radical polymerization step of performing radical polymerization using the radically polymerizable raw material composition after completion of the polyaddition reaction step and the radically polymerizable raw material composition-preparing step, to thereby form a polyurethane-based composite material, wherein a polymerizable monomer blending ratio Rr represented by the following equation (1) is from 20 mass % to 80 mass %:

$$Rr=100\times Br/[a1r+a2r+Ar+Br] \quad \text{Equation (1)}$$

in the equation (1), a1r represents a content (parts by mass) of the diol compound (a1) remaining unreacted in the radically polymerizable raw material composition, a2r represents a content (parts by mass) of the diisocyanate compound (a2) remaining unreacted in the radically polymerizable raw material composition, Ar represents a content (parts by mass) of the polyurethane component (A) in the radically polymerizable raw material composition, and Br represents a content (parts by mass) of the polymerizable monomer (B) in the radically polymerizable raw material composition.

In addition, in the following description, the diol compound having one or more radically polymerizable groups is sometimes referred to as "radically polymerizable diol compound," the polyurethane component having a number average molecular weight of from 1,500 to 5,000 and having a radically polymerizable group is sometimes referred to as "radically polymerizable polyurethane component," and the polymerizable monomer having one or more radically polymerizable groups in the molecule, and being free from causing a polyaddition reaction with any of the diol compound (a1) and the diisocyanate compound (a2) is sometimes referred to as "non-polyadding radically polymerizable monomer."

In the method of producing a polyurethane-based composite material according to this embodiment, a cured body (polyurethane-based composite material) excellent not only in strength and water resistance but also in uniformity can be easily produced. The reason why such effect is obtained cannot be definitely identified, but the inventors of the present invention presume that the reason is as described below.

First, in the method of producing a polyurethane-based composite material according to this embodiment, the radically polymerizable groups of the components each having a radically polymerizable group (i.e., the radically polymerizable polyurethane component (A) and the non-polyadding radically polymerizable monomer (B)) react with each other at the time of radical polymerization. In addition, the molecular size of the radically polymerizable polyurethane component (A) to be used in the radical polymerization is controlled to an appropriate size corresponding to a number average molecular weight of from 1,500 to 5,000. Accordingly, a large number of crosslinking points can be easily formed during the radical polymerization. Conceivably as a result of the foregoing, the strength and water resistance of the polyurethane-based composite material obtained through the radical polymerization are improved.

In the polyaddition reaction step of the technology described in U.S. Pat. No. 4,787,850 A, in addition to an isocyanate and a polyol serving as general polyurethane precursor components, a third main component, i.e., a methacrylate monomer having two or more hydroxyl groups (being both a polyurethane precursor component and a polymerizable monomer) is also involved in the polyaddition reaction. In addition, in the technology described in JP 2002-527588 A, as polyurethane precursor components, an isocyanate and a monomer having a hydroxyl group and a radically polymerizable group (being both a polyurethane precursor component and a radically polymerizable monomer) are involved in the polyaddition reaction. That is, in each of the technologies described in U.S. Pat. No. 4,787,850 A and JP 2002-527588 A, the radically polymerizable monomer is incorporated as part of the polyurethane component (molecule having a relatively large size) formed through the polyaddition reaction. Accordingly, as a consequence, the formation of crosslinking points via radically polymerizable groups is restricted in the radical polymerization step serving as the next step.

However, in the method of producing a polyurethane-based composite material according to this embodiment, the non-polyadding radically polymerizable monomer (B) contained in the polyaddition-reactive raw material composition to be used in the polyaddition reaction step is not involved in the polyaddition reaction. Accordingly, in the radical polymerization step serving as the next step, the non-polyadding radically polymerizable monomer (B) can easily approach the radically polymerizable group of the radically polymerizable polyurethane component (A), which is a molecule having a relatively large size, to undergo radical polymerization, and hence the formation of crosslinking points through the radical polymerization is hardly inhibited. For such reason, it is conceived that, in the method of producing a polyurethane-based composite material according to this embodiment, a polyurethane-based composite material excellent in strength and water resistance can be more easily obtained than in the technologies described in U.S. Pat. No. 4,787,850 A and JP 2002-527588 A.

Meanwhile, the inventors of the present invention have investigated the cause of a reduction in uniformity of the produced cured body in the technology described in JP 2019-210233 A. As a result, the inventors have found that the uniformity of the cured body results from the control states of the polyaddition reaction and the radical polymerization. That is, in the technology described in JP 2019-210233 A, the polyaddition reaction and the radical polymerization are carried out simultaneously in parallel with each other over time, and hence it is difficult to control the two reactions separately and individually. It is conceived that, owing to the difficulty in controlling the reactivities of the two reactions as just described, in the technology described in JP 2019-210233 A, the uniformity of the cured body is liable to be reduced through, for example, the occurrence of polymerization shrinkage as a result. In view of this, in the method of producing a polyurethane-based composite material according to this embodiment, the polyaddition reaction and the radical polymerization are controlled separately and individually by carrying out the radical polymerization step after the completion of the polyaddition reaction step. Accordingly, the uniformity of the cured body to be obtained can be easily secured.

Now, various raw materials to be used in the method of producing a polyurethane-based composite material according to this embodiment, the steps thereof, and the like are described in detail.

2. Various Raw Materials to be Used in Method of Producing Polyurethane-Based Composite Material 2-1. Radically Polymerizable Diol Compound (a1)

The radically polymerizable diol compound (a1) is a compound serving as a raw material for forming the radically polymerizable polyurethane component (A). In addition, the two hydroxyl groups of the radically polymerizable diol compound (a1) and the isocyanate groups of the diisocyanate compound (a2) serving as the other polyurethane precursor component cause a polyaddition reaction in the polyaddition reaction step, to thereby form the radically polymerizable polyurethane component (A).

A compound having at least one radically polymerizable group and two hydroxyl groups in the molecule may be used as the radically polymerizable diol compound (a1) without any particular limitation. Herein, the "radically polymerizable group" means a functional group that is caused to react and polymerize by an initiator that generates a radical, and specifically means a group having a radically polymerizable carbon-carbon double bond, such as a vinyl group, a (meth) acrylate group, and a styryl group.

By virtue of the diol compound having a radically polymerizable group, the radically polymerizable group is introduced into the main chain of the polyurethane molecule to be formed through the polyaddition reaction. In addition, during the radical polymerization in the radical polymerization step, a bond is formed through a reaction between the radically polymerizable groups in the molecules of the radically polymerizable polyurethane component (A), or between the radically polymerizable group in the molecule of the radically polymerizable polyurethane component (A) and the radically polymerizable group of the non-polyadding radically polymerizable monomer (B), and thus a crosslink is formed. Thus, the water resistance of the polyurethane-based composite material that is the cured body is improved.

In the radically polymerizable polyurethane component (A), the radically polymerizable group is preferably a (meth) acrylate group from the viewpoint that urethane (meth) acrylate capable of forming a hydrogen bond to enhance toughness can be formed. From the viewpoints of the strength and water resistance of the polyurethane-based composite material as a product, the number of radically polymerizable groups contained in the molecule of the radically polymerizable diol compound (a1) is preferably from 1 to 4, particularly preferably 1 or 2. When the number of radically polymerizable groups is set to 4 or less, the shrinkage of the cured body to be formed at the time of the radical polymerization reaction can be more easily suppressed.

In addition, the number of constituent atoms of a main chain in a divalent organic residue interposed between the two hydroxyl groups contained in the molecule of the radically polymerizable diol compound (a1) (hereinafter sometimes referred to as "OH-to-OH distance") is preferably from 2 to 8, more preferably from 2 to 6, particularly preferably from 2 to 4. When the OH-to-OH distance of the radically polymerizable diol compound (a1) is set to fall within the above-mentioned ranges, the radically polymerizable group can be introduced at a high density into the molecule of the radically polymerizable polyurethane component (A) to be obtained in the polyaddition reaction step, and moreover, while the strength of the polyurethane-based composite material is maintained, its bonding properties can also be easily enhanced.

When two or more kinds of the radically polymerizable diol compounds (a1) are used, the OH-to-OH distance means a value calculated as an average value for the two or more kinds of radically polymerizable diol compounds (a1). In this case, the average value of the OH-to-OH distance is calculated on the basis of the following equation (2) when "n" kinds of the radically polymerizable diol compounds (a1) are used.

$$\text{Average value of } OH\text{-to-}OH \text{ distance} = \sum_{x=1}^{n}(Dx \times Mx) \qquad \text{Equation (2)}$$

In the equation (2), "n" represents an integer of 2 or more, "x" represents an integer in the range of from 1 to "n", Dx represents the OH-to-OH distance of an x-th kind of radically polymerizable diol compound (a1), and Mx represents the molar fraction (mol/mol) of the x-th radically polymerizable diol compound (a1) in the case where the total amount of 1st to n-th radically polymerizable diol compounds (a1) is 1 mol.

Examples of the compound suitably used as the radically polymerizable diol compound (a1) may include trimethylolpropane mono(meth)acrylate, glycerol mono(meth)acrylate, pentaerythritol di(meth)acrylate, and a ring-opened product of ethylene glycol diglycidyl ether with an acid ((meth)acrylic acid or vinylbenzoic acid). Those compounds may be used alone or as a mixture thereof.

2-2. Diisocyanate Compound (a2)

The diisocyanate compound (a2) is the other polyurethane precursor component for forming the radically polymerizable polyurethane component (A), and a known compound having two isocyanate groups in one molecule may be used without any particular limitation.

Examples of the compound suitably used as the diisocyanate compound (a2) may include 1,3-bis(2-isocyanato-2-propyl)benzene, 2,2-bis(4-isocyanatophenyl)hexafluoropropane, 1,3-bis(isocyanatomethyl)cyclohexane, methylenediphenyl 4,4'-diisocyanate, 3,3'-dichloro-4,4'-diisocyanatobiphenyl, 4,4'-diisocyanato-3,3'-dimethylbiphenyl, dicyclohexylmethane 4,4'-diisocyanate, pentamethylene diisocyanate, hexamethylene diisocyanate, norbornane diisocyanate, isophorone diisocyanate, 1,5-diisocyanatonaphthalene, 1,3-phenylene diisocyanate, trimethylhexamethylene diisocyanate, tolylene-2,4-diisocyanate, tolylene-2,6-diisocyanate, and m-xylylene diisocyanate.

The diisocyanate compound (a2) is preferably a diisocyanate compound (a2) having a phenyl group in the molecule, particularly preferably m-xylylene diisocyanate, out of those compounds, from the viewpoints of the operability of the radically polymerizable raw material composition and the strength of the polyurethane-based composite material to be obtained.

The use amounts of the radically polymerizable diol compound (a1) and the diisocyanate compound (a2) in the polyaddition reaction step are not particularly limited as long as their molar ratio (use amount of diisocyanate compound (a2)/use amount of radically polymerizable diol compound (a1)) is around 1 mol/mol, but it is generally preferred that the molar ratio be from about 0.9 mol/mol to about 1.2 mol/mol. From the viewpoint that, in the polyaddition reaction step, the radically polymerizable diol compound (a1) and the diisocyanate compound (a2) react quantitatively to form the radically polymerizable polyurethane component (A) and to reduce the amount of an unreacted substance to the extent possible, the molar ratio is preferably from 1.0 mol/mol to 1.1 mol/mol.

2-3. Radically Polymerizable Polyurethane Component (A)

The radically polymerizable polyurethane component (A) is a component formed through the polyaddition reaction between the radically polymerizable diol compound (a1) and the diisocyanate compound (a2) in the polyaddition reaction step. In addition, the structure of the radically polymerizable polyurethane component (A) is almost unambiguously determined by the radically polymerizable diol compound (a1) and the diisocyanate compound (a2) used in the polyaddition reaction step.

In addition, the radically polymerizable polyurethane component (A) is also a component that undergoes radical polymerization with the non-polyadding radically polymerizable monomer (B) through the catalytic action of the radical polymerization initiator (C), to thereby serve as a component of a polyurethane-based resin matrix in the polyurethane-based composite material that is a final product. Accordingly, with the exclusion of the filler (D), the rest of the components of the radically polymerizable raw material composition, namely components including the radically polymerizable polyurethane component (A), the non-polyadding radically polymerizable monomer (B), and the radical polymerization initiator (C) as main components may be called a matrix raw material composition. In the case where the radically polymerizable raw material composition further contains a fifth component in addition to the components A to D, when the fifth component dissolves in the radically polymerizable polyurethane component (A) and/or the non-polyadding radically polymerizable monomer (B), the fifth component also serves as a component of the matrix raw material composition.

The radically polymerizable polyurethane component (A) contained in the radically polymerizable raw material composition has a number average molecular weight of from 1,500 to 5,000. By virtue of setting the number average molecular weight to 1,500 or more, a polyurethane-based composite material having sufficient strength can be obtained. Meanwhile, the inventors of the present invention have made various attempts to obtain a radically polymerizable polyurethane component (A) having a number average molecular weight of more than 5,000 by subjecting the diol compound (a1) and the diisocyanate compound (a2) to a polyaddition reaction in polyaddition-reactive raw material compositions prepared with varied values for the content of the non-polyadding radically polymerizable monomer (B), but have been unable to obtain a radically polymerizable polyurethane component (A) having a number average molecular weight of more than 5,000. Accordingly, from the viewpoints of producibility and practicality, it is appropriate that the number average molecular weight be 5,000 or less. When the number average molecular weight is made smaller while the number average molecular weight falls within the range of from 1,500 to 5,000, the precipitation of the radically polymerizable polyurethane component (A) into the matrix raw material composition is more reliably suppressed to further facilitate uniform radical polymerization. Besides, when the radically polymerizable raw material composition is paste-like, the radically polymerizable raw material composition is also improved in fluidity and reduced in viscosity, and hence its operability is further improved. From the viewpoint of achieving both the operability of the radically polymerizable raw material composition and the strength of the polyurethane-based composite material in a well-balanced manner, the number average molecular weight is preferably from 1,500 to 3,500, more preferably from 1,700 to 3,300, particularly preferably from 2,000 to 3,000. In addition, the radically polymerizable polyurethane component (A) is preferably soluble in the non-polyadding radically polymerizable monomer (B) in the matrix raw material composition at least at a temperature at which the radical polymerization reaction in the radical polymerization step is performed.

In the polyaddition reaction in the polyaddition reaction step of the method of producing a polyurethane-based composite material according to this embodiment, the non-polyadding radically polymerizable monomer (B), which is not involved in the polyaddition reaction, functions as a solvent, and hence a polyurethane having such a high molecular weight as to cause a precipitate is not formed. In addition, the presence of the non-polyadding radically polymerizable monomer (B) functioning as a solvent influences the collision frequency (reaction opportunity) between the radically polymerizable diol compound (a1) and the diisocyanate compound (a2) that are present in the reaction system, and hence the number average molecular weight can be adjusted to the above-mentioned ranges by adjusting the blending amount of the non-polyadding radically polymerizable monomer (B) in the polyaddition-reactive raw material composition. In this case, the number average molecular weight can be reduced by increasing the content ratio of the non-polyadding radically polymerizable monomer (B) in the polyaddition-reactive raw material composition, and the number average molecular weight can be increased by reducing the content ratio.

The number average molecular weight of the radically polymerizable polyurethane component (A) means a number average molecular weight in terms of polystyrene determined by gel permeation chromatography (GPC) measurement. The number average molecular weight of the radically polymerizable polyurethane component (A) in the radically polymerizable raw material composition may be determined by performing GPC measurement for a solution obtained by adding a solvent such as tetrahydrofuran (THF) to the radically polymerizable raw material composition as required and removing an insoluble component such as the filler (D) through an operation, such as filtration or centrifugation (i.e., a solution formed of the matrix raw material composition, or of a mixture of the matrix raw material composition and the solvent added as required). The measurement may be performed using Advanced Polymer Chromatography (manufactured by Nihon Waters K.K.) under the following measurement conditions.

[Measurement Conditions]

Columns: ACQUITY APC™ XT 45, 1.7 μm
ACQUITY APC™ XT 125, 2.5 μm
Column temperature: 40° C.
Developing solvent: THF
Flow rate: 0.5 ml/min
Detector: a photodiode array detector at 254 nm (PDA detector)

2-4. Non-Polyadding Radically Polymerizable Monomer (B)

The non-polyadding radically polymerizable monomer (B) is a compound having at least one radically polymerizable group in the molecule, and being free from causing a polyaddition reaction with any of the radically polymerizable diol compound (a1) and the diisocyanate compound (a2). Herein, "being free from causing a polyaddition reaction with any of the radically polymerizable diol compound (a1) and the diisocyanate compound (a2)" means containing in the molecule neither a group that causes a polyaddition reaction with the radically polymerizable diol compound (a1) nor a group that causes a polyaddition reaction with the diisocyanate compound (a2), and specifically means containing none of a hydroxyl group, an amino group, a carboxy group, an isocyanate group, and a mercapto group. The group capable of causing a polyaddition reaction with the radically polymerizable diol compound (a1) is, for example, an isocyanate group out of those functional groups, and the group capable of causing a polyaddition reaction with the diisocyanate compound (a2) is, for example, a hydroxyl group, an amino group, a carboxyl group, or a mercapto group out of those functional groups. Accordingly, the non-polyadding radically polymerizable monomer (B) has none of a hydroxyl group, an amino group, a carboxy group, an isocyanate group, and a mercapto group in the molecule. In addition, as the radically polymerizable group, there may be utilized a group similar to the radically polymerizable group of the radically polymerizable diol compound (a1). As a suitable radically polymerizable group, a (meth)acrylate group and/or a (meth)acrylamide group, or a group having a molecular structure identical to that of the radically polymerizable group of the radically polymerizable diol compound (a1) is preferred. The number of radically polymerizable groups contained in the molecule of the non-polyadding radically polymerizable monomer (B) is preferably from 2 to 6, more preferably from 2 to 4, from the viewpoint of the ease with which crosslinks are formed. When the number of radically polymerizable groups is set to 2 or more, a crosslink density can be further increased, and hence a cured body having sufficient strength can be more easily obtained. In addition, when the number of radically polymerizable groups is set to 6 or less, shrinkage at the time of curing can be more easily suppressed. In addition, the non-polyadding radically polymerizable monomer (B) is preferably liquid at room temperature (i.e., 25° C.).

The non-polyadding radically polymerizable monomer (B) in the polyaddition-reactive raw material composition is not involved in the polyaddition reaction in the polyaddition reaction step, and functions as a solvent. Accordingly, the number average molecular weight of the radically polymerizable polyurethane component (A) to be formed in the polyaddition reaction step can be extremely easily adjusted to fall within the range of from 1,500 to 5,000. In addition, the non-polyadding radically polymerizable monomer (B) in the radically polymerizable raw material composition (i) accelerates the dispersion of the radically polymerizable polyurethane component (A) to contribute to an improvement in operability of the radically polymerizable raw material composition when the phase form of the radically polymerizable raw material composition is paste-like, and (ii) also contributes to the formation of a crosslinking point because part of the non-polyadding radically polymerizable monomer (B) reacts with the radically polymerizable group of the radically polymerizable polyurethane component (A) to form a bond in the radical polymerization step.

The viscosity of the non-polyadding radically polymerizable monomer (B) is not particularly limited, but falls within preferably the range of from 1 mPa·s to 1,000 mPa·S, more preferably the range of from 1 mPa·s to 100 mPa·s at ordinary temperature. When the phase form of the radically polymerizable raw material composition is paste-like, the operability of the radically polymerizable raw material composition can be further improved by using a non-polyadding radically polymerizable monomer (B) having a viscosity in the above-mentioned ranges.

A polymerizable monomer represented by the following structural formula (1) is preferably incorporated as the non-polyadding radically polymerizable monomer (B) for the reason that the number average molecular weight of the radically polymerizable polyurethane component (A) can be easily adjusted to fall within the range of from 1,500 to 5,000.

(1)

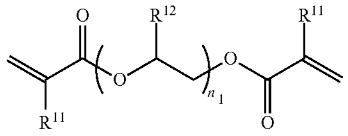

In the structural formula (1), $R^{11}$ and $R^{12}$ each represent a hydrogen atom or a methyl group, and $n_1$ represents an integer of from 1 to 10, preferably an integer of from 1 to 3.

Examples of the compound that may be suitably used as the non-polyadding radically polymerizable monomer (B) may include ethylene glycol di(meth)acrylate, diethylene glycol di(meth)acrylate, triethylene glycol di(meth)acrylate, polyethylene glycol methacrylate, polypropylene glycol methacrylate, tricyclodecanol methacrylate, trimethylolpropane methacrylate, pentaerythritol methacrylate, ditrimethylolpropane methacrylate, and dipentaerythritol methacrylate. Of those, ethylene glycol di(meth)acrylate, diethylene glycol di(meth)acrylate, and triethylene glycol di(meth) acrylate are particularly preferred.

The content of the non-polyadding radically polymerizable monomer (B) in the radically polymerizable raw material composition needs to be from 20 mass % to 80 mass % in terms of polymerizable monomer blending ratio Rr represented by the equation (1). By virtue of setting the polymerizable monomer blending ratio Rr to 80 mass % or less, the content ratio of the radically polymerizable polyurethane component (A), which contributes to an improvement in strength, can be increased to provide a polyurethane-based composite material having sufficient strength. In addition, by virtue of setting the polymerizable monomer blending ratio Rr to 20 mass % or more, the homogeneity of the radically polymerizable raw material composition is increased, and hence, as a consequence, curing unevenness of the cured body to be obtained can be suppressed to provide a cured body excellent in uniformity. Besides, when the phase form of the radically polymerizable raw material composition is paste-like, its operability can also be easily improved. From the viewpoint of achieving both the suppression of curing unevenness of the cured body and the strength of the cured body in a more balanced manner, the polymerizable monomer blending ratio Rr is preferably from 20 mass % to 50 mass %, more preferably from 20 mass % to 35 mass %. Further, from the viewpoint that a polyurethane-based composite material that is also excellent in bonding properties can be easily obtained, the polymerizable monomer blending ratio Rr is particularly preferably from 20 mass % to 35 mass %.

2-5. Radical Polymerization Initiator (C)

The radical polymerization initiator (C) has a function of initiating the radical polymerization reaction in the radical polymerization step, and has a function of causing radically polymerizable groups to react with each other and be bonded to each other, to thereby polymerize and cure the radically polymerizable raw material composition and form crosslinking points. A thermal radical polymerization initiator and/or a photoradical polymerization initiator may be used as the radical polymerization initiator (C), but a thermal radical polymerization initiator is preferably used from the standpoint that the radically polymerizable raw material composition can be uniformly cured to the inside. From the viewpoints of ease of handling and stability, the thermal polymerization initiator is preferably a thermal polymerization initiator having a 10-hour half-life temperature in the range of from 40° C. to 150° C., and particularly suitably has a 10-hour half-life temperature in the range of from 70° C. to 100° C. Herein, the "10-hour half-life temperature" refers to a temperature at which the presence amount of the thermal polymerization initiator is reduced to half of its initial level after a lapse of 10 hours from the initial stage, and is used as an indicator of the reactivity of the thermal polymerization initiator. Specific examples of the thermal radical polymerization initiator that may be suitably used may include: peroxide initiators, such as benzoyl peroxide and tert-butyl peroxylaurate; and azo-based initiators, such as azobisbutyronitrile and azobis(2,4-dimethylvaleronitrile). Those thermal polymerization initiators may be used alone or as a mixture thereof.

The use amount of the radical polymerization initiator (C) only needs to be appropriately decided in accordance with the kind thereof, but generally falls within preferably the range of from 0.005 mass % to 2.0 mass %, more preferably the range of from 0.01 mass % to 1.0 mass % with respect to the mass of the matrix raw material composition.

2-6. Filler (D)

The filler (D) has a function of improving the physical properties, such as mechanical strength, abrasion resistance, and water resistance, of the polyurethane-based composite material by being dispersed in the polyurethane-based resin matrix and composited with the polyurethane-based resin matrix.

An inorganic filler, such as silica, alumina, titania, zirconia, or a composite oxide thereof, or glass, is preferably used as the filler (D). Specific examples of such inorganic filler may include spherical-shaped particles or irregular-shaped particles of amorphous silica, silica-zirconia, silica-titania, silica-titania-zirconia, quartz, alumina, and the like. When the polyurethane-based composite material produced by the method of producing a polyurethane-based composite material according to this embodiment is utilized as a dental material, silica, titania, zirconia, or a composite oxide thereof is preferably used as the filler (D), and silica or a composite oxide thereof is particularly preferred. This is because any such inorganic filler is free of a risk of dissolving in an environment in the mouth and allows easy adjustment of a difference between its refractive index and that of the polyurethane-based resin matrix, thus facilitating the control of transparency and aesthetics.

The shape of the filler (D) is not particularly limited, and may be appropriately selected in accordance with an application of the polyurethane-based composite material of interest, but for example, a spherical shape is suitable from the viewpoint that a polyurethane-based composite material particularly excellent in abrasion resistance, surface smoothness, and gloss retention is obtained. In addition, a polyurethane-based composite material having the filler (D) of a spherical shape dispersed and incorporated therein is also particularly suitable in a dental application. As used herein, the term "spherical shape" means that an average degree of symmetry determined in image analysis of an image taken with a scanning or transmission electron microscope is 0.6 or more. The average degree of symmetry is more preferably 0.7 or more, still more preferably 0.8 or more. The average degree of symmetry may be calculated by measuring a long diameter (L) that is the maximum diameter and a short diameter (B) orthogonal to the long diameter (L) for each of "n" (generally 40 or more, preferably 100 or more) particles in image analysis of an image taken with a scanning or transmission electron microscope, determining a ratio therebetween (B/L), and dividing the summation of the ratios ($\Sigma B/L$) by "n".

The average particle diameter of the filler (D) is preferably from 0.001 μm to 100 μm, more preferably from 0.01 μm to 10 μm, from the viewpoints of abrasion resistance, surface smoothness, and gloss retention. In addition, from the standpoint that the content ratio of the filler (D) in the polyurethane-based composite material can be easily improved, a filler (D) having a plurality of particle diameters is preferably used. Specifically, a particle diameter of from 0.001 μm to 0.1 μm and a particle diameter of from 0.1 μm to 100 μm are preferably combined, and a particle diameter of from 0.01 μm to 0.1 μm and a particle diameter of from 0.1 μm to 10 μm are more preferably combined.

The filler (D) is preferably subjected to surface treatment before use in order to improve its affinity for the polyurethane-based resin matrix to improve the mechanical strength and water resistance of the polyurethane-based composite material. A silane coupling agent is generally used as a surface treatment agent, and in particular, in an inorganic particle-based filler (D) containing silica as a base, for example, methyltrimethoxysilane, methyltriethoxysilane, vinyltrimethoxysilane, 3-methacryloyloxypropyltrimethoxysilane, 3-glycidoxypropyltrimethoxysilane, and 2-(3,4-epoxycyclohexyl)ethyltrimethoxysilane are each suitably used as a silane coupling agent having a high effect of surface treatment with the silane coupling agent.

The use amount of the filler (D) only needs to be appropriately decided in accordance with the physical properties such as strength of the polyurethane-based composite material of interest, but from the viewpoint of increasing the strength of the polyurethane-based composite material, is preferably from 60 mass % to 85 mass %, more preferably from 65 mass % to 80 mass % as expressed in mass % with respect to the mass of the radically polymerizable raw material composition (hereinafter sometimes referred to simply as "filling ratio"). In addition, when the polyurethane-based composite material produced by the method of producing a polyurethane-based composite material according to this embodiment is used as a material for dental cutting work, the filling ratio is more preferably from 65 mass % to 80 mass %, still more preferably from 70 mass % to 80 mass %.

The inventors of the present invention have attempted to produce a polyurethane-based composite material in which the blending amount of the filler (D) is more than 60 mass % through utilization of the technology described in JP 2019-210233 A. However, it has been found that, even when a paste-like raw material composition prepared for the production of such polyurethane-based composite material is used, a period of time for which the raw material composition exhibits a paste state suited for its pouring into a mold is extremely reduced. Besides, it has also been found that, in this case, the raw material composition is difficult to pour into the mold and form into a desired shape, or even when the raw material composition can be poured into the mold, a uniform cured body cannot be obtained because defoaming cannot be sufficiently performed. However, when the method of producing a polyurethane-based composite material according to this embodiment is utilized in combination with a forming method involving using a mold, a uniform cured body can be easily produced even in the case of a polyurethane-based composite material having a high filling ratio of more than 60 mass %.

2-7. Other Additives

The radically polymerizable raw material composition or the polyaddition-reactive raw material composition may have blended therein other various additives in addition to the essential components described above. Examples of the various additives may include a polymerization inhibitor, a fluorescent agent, an ultraviolet absorber, an antioxidant, a pigment, an antibacterial agent, and an X-ray contrast agent. The addition amounts thereof only need to be appropriately decided in accordance with a desired purpose.

3. Steps of Method of Producing Polyurethane-Based Composite Material

The method of producing a polyurethane-based composite material according to this embodiment includes the polyaddition reaction step, the radically polymerizable raw material composition-preparing step, and the radical polymerization step. Details of the steps are described below.

3-1. Polyaddition Reaction Step (1) Preparation of Polyaddition-Reactive Raw Material Composition In the polyaddition reaction step, first, the polyaddition-reactive raw material composition containing the radically polymerizable diol compound (a1), the diisocyanate compound (a2), and the non-polyadding radically polymerizable monomer (B) is prepared. Then, in the polyaddition-reactive raw material composition, a polyaddition reaction between the radically polymerizable diol compound (a1) and the diisocyanate compound (a2) is carried out to form the radically polymerizable polyurethane component (A).

The polyaddition-reactive raw material composition may further contain a component other than the above-mentioned three kinds of components. For example, in the case where the filling ratio of the filler (D) in the radically polymerizable raw material composition is high (e.g., the case where the filling ratio is about 60 mass % or more), from a first viewpoint of making it easier to secure the uniformity of the cured body to be obtained, and to secure the operability of each of the polyaddition-reactive raw material composition and the radically polymerizable raw material composition in the course of preparing these raw material compositions, it is preferred that (i) the polyaddition-reactive raw material composition further contain the filler (D) in addition to the radically polymerizable diol compound (a1), the diisocyanate compound (a2), and the non-polyadding radically polymerizable monomer (B). In addition, from the above-mentioned first viewpoint and a second viewpoint that the radically polymerizable raw material composition can also be prepared simultaneously with the completion of the polyaddition reaction, it is more preferred that (ii) the polyaddition-reactive raw material composition further contain the radical polymerization initiator (C) and the filler (D) in addition to the radically polymerizable diol compound (a1), the diisocyanate compound (a2), and the non-polyadding radically polymerizable monomer (B). When the polyaddition-reactive raw material composition is according to the embodiment described in (ii) above, the polyaddition reaction step and the radically polymerizable raw material composition-preparing step can be simultaneously completed.

In addition, a preparation procedure for the polyaddition-reactive raw material composition is not particularly limited, and the polyaddition-reactive raw material composition may be prepared by any preparation procedure. As the preparation procedure for the polyaddition-reactive raw material composition, there is given (a) a single-stage preparation method in which the polyaddition-reactive raw material composition is prepared by mixing all the constituent components of the polyaddition-reactive raw material composition at one time, or (b) a multistage preparation method in which the polyaddition-reactive raw material composition is prepared by preparing a mixed composition having mixed therein part of the constituent components of the polyaddition-reactive raw material composition, and then adding and mixing the rest of the constituent components of the polyaddition-reactive raw material composition into the mixed composition at one time or sequentially adding and mixing the rest of the constituent components into the mixed composition in a plurality of divided portions. Which preparation method to adopt may be appropriately selected in comprehensive consideration of, for example, the composition and operability of the polyaddition-reactive raw material composition to be prepared, compatibility among the constituent components of the polyaddition-reactive raw material composition, and working efficiency in preparing the polyaddition-reactive raw material composition.

The blending ratio of the non-polyadding radically polymerizable monomer (B) in the polyaddition-reactive raw material composition is not particularly limited, but is preferably from 20 mass % to 80 mass %, more preferably from 20 mass % to 50 mass % in terms of polymerizable monomer blending ratio Rp represented by the following equation (1').

$$Rp=100\times Bp/[a1p+a2p+Bp] \quad \text{Equation (1')}$$

In the equation (1'), a1p represents the content (parts by mass) of the radically polymerizable diol compound (a1) in the polyaddition-reactive raw material composition, a2p represents the content (parts by mass) of the diisocyanate compound (a2) in the polyaddition-reactive raw material composition, and Bp represents the content (parts by mass) of the non-polyadding radically polymerizable monomer (B) in the polyaddition-reactive raw material composition.

When the polymerizable monomer blending ratio Rp is set to from 20 mass % to 80 mass %, the operability of the polyaddition-reactive raw material composition is improved, and moreover, the number average molecular weight of the radically polymerizable polyurethane component (A) to be produced through the polyaddition reaction can be extremely easily controlled to fall within the range of from 1,500 to 5,000. In addition, before and after the polyaddition reaction step is carried out, the total mass of the radically polymerizable diol compound (a1), the diisocyanate compound (a2), and the radically polymerizable polyurethane component (A) that are present in the reaction system does not change. Accordingly, when a polyaddition-reactive raw material composition in which the polymerizable monomer blending ratio Rp is set to from 20 mass % to 80 mass % is used, a radically polymerizable raw material composition in which the polymerizable monomer blending ratio Rr is from 20 mass % to 80 mass % can be extremely easily prepared. This is because, when the composition that has completed the polyaddition reaction step is used as it is as the radically polymerizable raw material composition, the following relationship is established: polymerizable monomer blending ratio Rp=polymerizable monomer blending ratio Rr.

When the polyaddition reaction step is carried out using a polyaddition-reactive raw material composition in which the polymerizable monomer blending ratio Rp is less than 20 mass %, the polymerizable monomer blending ratio Rr may be adjusted so as to fall within the range of from 20 mass % to 80 mass % after the completion of the polyaddition reaction step. For example, when the polyaddition reaction step is carried out using a polyaddition-reactive raw material composition in which the polymerizable monomer blending ratio Rp is less than 20 mass %, the polymerizable monomer blending ratio Rr may be adjusted so as to become 20 mass % or more by additionally adding the non-polyadding radically polymerizable monomer (B) after the completion of the polyaddition reaction step.

In the case where the following conditions 1 and 2 are satisfied, (b) the multistage preparation method is suitably adopted from the viewpoint of making it easier to secure the uniformity of the cured body to be obtained, and to secure the operability of each of the polyaddition-reactive raw material composition and the radically polymerizable raw material composition in the course of preparing these raw material compositions.

<1> The polyaddition-reactive raw material composition contains at least the radically polymerizable diol compound (a1), the diisocyanate compound (a2), the non-polyadding radically polymerizable monomer (B), and the filler (D).

<2> In the case where the filling ratio of the filler (D) in the radically polymerizable raw material composition is high (e.g., the filling ratio is about 60 mass % or more).

Now, as a preparation example of the polyaddition-reactive raw material composition, an example of a procedure for preparing the polyaddition-reactive raw material composition by the multistage preparation method is described. In this case, first, the radically polymerizable diol compound (a1), the non-polyadding radically polymerizable monomer (B), and the filler (D) are at least mixed to prepare a primary raw material composition containing these components. The primary raw material composition may be prepared by mixing all the constituent components of the primary raw material composition at one time, or may be prepared by preparing a mixture having mixed therein part of the constituent components of the primary raw material composition, and then adding and mixing the rest of the constituent components of the primary raw material composition. The content of each component in the primary raw material composition may be appropriately selected so that a polyaddition-reactive raw material composition and a radically polymerizable raw material composition each having the target composition may be obtained. The preparation of the primary raw material composition is advantageous in: making it easier to secure the uniformity of the cured body to be obtained particularly in the case where the filling ratio of the filler (D) in the cured body to be produced is high; and obtaining excellent operability when the polyaddition-reactive raw material composition is paste-like.

In the preparation of the primary raw material composition, a mixing method for mixing the components with each other is not particularly limited, and a method involving using a magnetic stirrer, a mortar machine, a planetary mixer, a centrifugal mixer, or the like is appropriately used. In addition, for the reason that the filler (D) can be uniformly dispersed with ease, the primary raw material composition is preferably prepared by first mixing the radically polymerizable diol compound (a1) and the non-polyadding radically polymerizable monomer (B) to prepare a mixed composition, and then adding and mixing the filler (D) into the mixed composition. Further, from the standpoint that a side reaction can be easily suppressed and dispersion is facilitated, it is preferred that the radical polymerization initiator (C) be also added to the primary raw material composition. Similarly, it is preferred that any other additive be also added to the primary raw material composition. The thus prepared primary raw material composition is preferably subjected to defoaming treatment to eliminate air bubbles contained thereinside. A known method is used as a method for the defoaming, and a method, such as pressurizing defoaming, vacuum defoaming, or centrifugal defoaming, may be arbitrarily used. In addition, the diisocyanate compound (a2) is further added and mixed into the primary raw material composition. Thus, the polyaddition-reactive raw material composition may be prepared.

The polyaddition-reactive raw material composition (the primary raw material composition when the polyaddition-reactive raw material composition is prepared using the primary raw material composition) may further contain, as another additive, a catalyst for accelerating the polyaddition reaction as required, but may be free of any catalyst for accelerating the polyaddition reaction. Examples of the catalyst for accelerating the polyaddition reaction may include tin octylate and dibutyltin diacetate.

(2) Polyaddition Reaction

After the polyaddition-reactive raw material composition has been prepared, the radically polymerizable diol compound (a1) and the diisocyanate compound (a2) that are contained in the polyaddition-reactive raw material composition are subjected to a polyaddition reaction to form the radically polymerizable polyurethane component (A). The polyaddition reaction is initiated at the same time that the polyaddition-reactive raw material composition has been prepared, or by heating the polyaddition-reactive raw material composition as required. The polyaddition reaction is carried out so that the polyaddition reaction is allowed to progress until at least one of the radically polymerizable diol compound (a1) or the diisocyanate compound (a2) contained in the polyaddition-reactive raw material composition is substantially completely consumed by the polyaddition reaction, namely until the degree of progress of the polyaddition reaction reaches the vicinity of its maximum value (saturation value). Accordingly, when the polyaddition-reactive raw material composition is heated, a heating temperature and a heating time may be appropriately selected in view of the foregoing. In this case, the heating temperature is preferably from 30° C. to 100° C., more preferably from 35° C. to 80° C. In addition, from the viewpoint that the degree of progress of the polyaddition reaction can substantially reach the vicinity of its maximum value (saturation value), the heating time is: (1) preferably about 90 hours or more, more preferably about 100 hours or more when the heating temperature is 30° C. or more and less than 35° C.; (2) preferably about 65 hours or more, more preferably about 72 hours or more, still more preferably about 80 hours or more when the heating temperature is 35° C. or more and less than 50° C.; (3) preferably about 45 hours or more, more preferably about 55 hours or more, still more preferably about 65 hours or more when the heating temperature is 50° C. or more and less than 75° C.; and (4) preferably about 24 hours or more, more preferably about 35 hours or more, still more preferably about 45 hours or more when the heating temperature is 75° C. or more and 100° C. or less. In the above-mentioned cases (1) to (4), the upper limit value of the heating time is not particularly limited, but is preferably 168 hours or less from the viewpoint of practicality such as productivity.

When the polyaddition-reactive raw material composition contains the radical polymerization initiator (C), a method that substantially prevents the occurrence of a radical polymerization reaction during the polyaddition reaction is adopted (however, a radical polymerization reaction that inevitably occurs, though to a slight degree, even when such method is adopted is permitted in the method of producing a polyurethane-based composite material according to this embodiment). When the radical polymerization reaction also occurs in a remarkable manner during the polyaddition reaction, the radical polymerization step is substantially initiated before the completion of the polyaddition reaction step and the radically polymerizable raw material composition-preparing step, and hence the method of producing a polyurethane-based composite material according to this embodiment itself becomes impossible to carry out. However, by virtue of the adoption of the above-mentioned method, even when the polyaddition-reactive raw material composition contains the radical polymerization initiator (C), the radical polymerization step can be carried out after the completion of the polyaddition reaction step and the radically polymerizable raw material composition-preparing step.

The method that substantially prevents the occurrence of a radical polymerization reaction during the polyaddition reaction is not particularly limited, but for example, methods described in the following (1) and (2) are suitably adopted. That is, (1) when a photopolymerization initiator is used as the radical polymerization initiator (C), it is preferred to prepare the polyaddition-reactive raw material composition and carry out the polyaddition reaction under an environment free of irradiation with light having a wavelength at which the photopolymerization initiator is activated (activation light). In addition, (2) when a thermal polymerization initiator is used as the radical polymerization initiator (C), the polyaddition-reactive raw material composition is preferably prepared in a state of being kept at a temperature lower than the 10-hour half-life temperature of the thermal polymerization initiator by from 80° C. to 20° C., and the polyaddition-reactive raw material composition is more preferably prepared in a state of being kept at a temperature lower than the 10-hour half-life temperature of the thermal polymerization initiator by from 70° C. to 50° C.

When the polyaddition-reactive raw material composition is prepared by the multistage preparation method, the method described in (1) above is also applied to a raw material composition containing the photopolymerization initiator to be utilized for the preparation of the polyaddition-reactive raw material composition in the multistage preparation method (e.g., the primary raw material composition also containing the photopolymerization initiator), and the method described in (2) above is also applied to a raw material composition containing the thermal polymerization initiator to be utilized for the preparation of the polyaddition-reactive raw material composition in the multistage preparation method (e.g., the primary raw material composition also containing the thermal polymerization initiator).

In the preparation of each of the polyaddition-reactive raw material composition and the raw material composition (e.g., the primary raw material composition) to be utilized as required for the preparation of the polyaddition-reactive raw material composition, mixing means to be used for mixing the components with each other is not particularly limited, and known mixing means may be appropriately utilized. Examples of such mixing means may include a magnetic stirrer, a mortar machine, a planetary mixer, and a centrifugal mixer. In addition, in order to avoid the entrapment of air bubbles in the composition during the mixing, the mixing may be performed under a pressurized condition and/or under a vacuum condition.

3-2. Radically Polymerizable Raw Material Composition-Preparing Step (1) Preparation Procedure for Radically Polymerizable Raw Material Composition In the radically polymerizable raw material composition-preparing step, the radically polymerizable raw material composition containing the radically polymerizable polyurethane component (A), the non-polyadding radically polymerizable monomer (B), the radical polymerization initiator (C), and the filler (D) is prepared.

A preparation procedure for the radically polymerizable raw material composition is appropriately decided in accordance with the composition of the polyaddition-reactive raw material composition. In this case, the preparation procedure may be described by being divided into the following cases depending on which components the polyaddition-reactive raw material composition contains out of the five components (the radically polymerizable diol compound (a1), the diisocyanate compound (a2), the non-polyadding radically polymerizable monomer (B), the radical polymerization initiator (C), and the filler (D)) in a corresponding relationship with the four essential components contained in the radically polymerizable raw material composition (the radically polymerizable polyurethane component (A), the non-polyadding radically polymerizable monomer (B), the radical polymerization initiator (C), and the filler (D)): a case of containing components listed in <1> below; a case of containing components listed in <2> below; a case of containing components listed in <3> below; and a case of containing components listed in <4> below.

<1> Radically polymerizable diol compound (a1), diisocyanate compound (a2), non-polyadding radically polymerizable monomer (B), and radical polymerization initiator (C)

<2> Radically polymerizable diol compound (a1), diisocyanate compound (a2), non-polyadding radically polymerizable monomer (B), and filler (D)

<3> Radically polymerizable diol compound (a1), diisocyanate compound (a2), non-polyadding radically polymerizable monomer (B), radical polymerization initiator (C), and filler (D)

<4> Radically Polymerizable Diol Compound (a1), Diisocyanate Compound (a2), and Non-Polyadding Radically Polymerizable Monomer (B)

<First Preparation Procedure>

When the polyaddition-reactive raw material composition contains the components listed in <1> above, first, in the polyaddition-reactive raw material composition, the radically polymerizable diol compound (a1) and the diisocyanate compound (a2) are subjected to a polyaddition reaction to form the radically polymerizable polyurethane component (A), and thus the polyaddition reaction step is completed. After that, the filler (D) is added and mixed into the intermediate composition containing the radically polymerizable polyurethane component (A), the non-polyadding radically polymerizable monomer (B), and the radical polymerization initiator (C). Thus, the radically polymerizable raw material composition may be prepared. In the first preparation procedure, the polyaddition reaction step and the radically polymerizable raw material composition-preparing step are carried out in the stated order.

<Second Preparation Procedure>

When the polyaddition-reactive raw material composition contains the components listed in <2> above, first, in the polyaddition-reactive raw material composition, the radically polymerizable diol compound (a1) and the diisocyanate compound (a2) are subjected to a polyaddition reaction to form the radically polymerizable polyurethane component (A), and thus the polyaddition reaction step is completed. After that, the radical polymerization initiator (C) is added and mixed into the intermediate composition containing the radically polymerizable polyurethane component (A), the non-polyadding radically polymerizable monomer (B), and the filler (D). Thus, the radically polymerizable raw material composition may be prepared.

Also in the second preparation procedure, the polyaddition reaction step and the radically polymerizable raw material composition-preparing step are carried out in the stated order. In addition, in the second preparation procedure, the radical polymerization initiator (C) is added and mixed into the intermediate composition obtained through the polyaddition reaction step, and hence there is no need to adopt the method that substantially prevents the occurrence of a radical polymerization reaction during the polyaddition reaction as exemplified in (1) and (2) above.

<Third Preparation Procedure>

When the polyaddition-reactive raw material composition contains the components listed in <3> above, first, in the polyaddition-reactive raw material composition, the radically polymerizable diol compound (a1) and the diisocyanate compound (a2) are subjected to a polyaddition reaction to form the radically polymerizable polyurethane component (A), and thus the polyaddition reaction step is completed. In addition, through the completion of the polyaddition reaction step, the preparation of the radically polymerizable raw material composition containing all of the four essential components is also completed. That is, in the third preparation procedure, the radically polymerizable raw material composition-preparing step is also completed simultaneously with the completion of the polyaddition reaction step.

<Fourth Preparation Procedure>

When the polyaddition-reactive raw material composition contains the components listed in <4> above, first, in the polyaddition-reactive raw material composition, the radically polymerizable diol compound (a1) and the diisocyanate compound (a2) are subjected to a polyaddition reaction to form the radically polymerizable polyurethane component (A), and thus the polyaddition reaction step is completed. After that, the radical polymerization initiator (C) and the filler (D) are added and mixed into the intermediate composition containing the radically polymerizable polyurethane component (A) and the non-polyadding radically polymerizable monomer (B). Thus, the radically polymerizable raw material composition may be prepared. In the fourth preparation procedure, the polyaddition reaction step and the radically polymerizable raw material composition-preparing step are carried out in the stated order.

(2) Phase Form of Radically Polymerizable Raw Material Composition

Of the four essential constituent components of the radically polymerizable raw material composition, main components in terms of content are the radically polymerizable polyurethane component (A), the non-polyadding radically polymerizable monomer (B), and the filler (D). In this connection, the non-polyadding radically polymerizable monomer (B) is a low-molecular substance that is liquid at ordinary temperature. Besides, although the radically polymerizable polyurethane component (A) is a polymer, its number average molecular weight has a relatively small value of from 1,500 to 5,000 (that is, its molecular size is considerably small). Consequently, the radically polymerizable polyurethane component (A) can be easily dissolved without precipitating in the non-polyadding radically polymerizable monomer (B). Accordingly, unless the filling ratio of the filler (D) is excessively high, the radically polymerizable raw material composition to be used in the method of producing a polyurethane-based composite material according to this embodiment is generally present as a paste-like composition. In addition, when the phase form of the radically polymerizable raw material composition is paste-like, the radically polymerizable raw material composition in which the polymerizable monomer blending ratio Rr is from 20 mass % to 80 mass %, namely a radically polymerizable raw material composition containing a sufficient amount of a low-molecular-weight component (non-polyadding radically polymerizable monomer (B)) is also excellent in operability. From the viewpoint of more reliably making the phase form of the radically polymerizable raw material composition paste-like, the filling ratio of the filler (D) is generally preferably 85 mass % or less, more preferably 80 mass % or less.

In addition, the radically polymerizable raw material composition is a composition that is extremely stable in the vicinity of ordinary temperature unless the radical polymerization initiator (C) is activated through photoirradiation and/or heating treatment. Consequently, the viscosity of the paste-like radically polymerizable raw material composition is temporally kept constant over a long period of time. Accordingly, the paste-like radically polymerizable raw material composition can also continuously maintain excellent operability under an ordinary-temperature environment over an extremely long period of time from immediately after its preparation unless the radical polymerization initiator (C) is activated.

For such reason, when the radically polymerizable raw material composition is a paste-like composition, the radical polymerization step (curing step) can be carried out after the radically polymerizable raw material composition is poured into a mold. In this case, a cured body having desired dimensions and shape corresponding to the mold can be obtained. In addition, the curing of the radically polymerizable raw material composition after its pouring into a mold is caused only by radical polymerization. Accordingly, as compared to the technology described in JP 2019-210233 A, in which a cured body is formed through a process in which a polyaddition reaction and radical polymerization occur simultaneously in parallel with each other in a raw material composition after its pouring into a mold, when molding is utilized in the method of producing a polyurethane-based composite material according to this embodiment using the paste-like radically polymerizable raw material composition, polymerization shrinkage at the time of the curing can be suppressed, and as a result, a cured body having high dimensional and shape accuracy with small deviations with respect to the dimensions and shape of the mold can be easily obtained. When molding using a mold is performed, at least a thermal polymerization initiator is generally blended as the radical polymerization initiator (C) into the paste-like radically polymerizable raw material composition, and the radical polymerization step is carried out by performing at least heating.

3-3. Radical Polymerization Step (Curing Step)

The radical polymerization step (curing step) is carried out after the polyaddition reaction step and the radically polymerizable raw material composition-preparing step have been completed. In the radical polymerization step, radical polymerization is performed by activating the radical polymerization initiator (C) contained in the radically polymerizable raw material composition, and thus the radically polymerizable raw material composition is cured. Thus, a cured body formed of a polyurethane-based composite material is obtained. When a thermal radical polymerization initiator is used as the radical polymerization initiator (C), the radical polymerization is caused to progress by heating the radically polymerizable raw material composition, and when a photoradical polymerization initiator is used as the radical polymerization initiator (C), the radical polymerization is caused to progress by irradiating the radically polymerizable raw material composition with light for activating the initiator.

Heat is generated due to the heat of reaction at the time of the radical polymerization, and hence it is preferred to control a heating temperature (curing temperature) during the heating in the case of using a thermal radical polymerization initiator as the radical polymerization initiator (C). In this case, the heating temperature is preferably controlled so as not to exceed 150° C., and the radical polymerization is particularly preferably performed at from −10° C. to +25° C. with respect to the 10-hour half-life temperature of the thermal radical polymerization initiator, that is, within the following range with respect to the 10-hour half-life temperature represented by T (° C.): from a temperature (lower limit temperature L) lower than the 10-hour half-life temperature T by 10° C. to a temperature (upper limit temperature H) higher than the 10-hour half-life temperature T by 25° C. When the heating temperature is set to be equal to or higher than the lower limit temperature L, the rate of the radical polymerization can be allowed to be sufficiently high, and moreover, the occurrence of unintended coloration of the cured body can also be easily suppressed. In addition, when the heating temperature is set to be equal to or lower than the upper limit temperature H, excessive consumption of radically polymerizable groups present in the reaction system can be prevented, and rapid progress of the radical polymerization can also be suppressed. When the heating temperature is controlled to fall within the above-mentioned temperature range, the polymerization and curing is allowed to progress at an industrially acceptable reaction rate, the occurrence of a strain or a crack in the cured body due to rapid progress of the reaction can also be suppressed, and moreover, the occurrence of deterioration of the non-poly-adding radically polymerizable monomer (B) can also be extremely easily suppressed. In addition, when the radical polymerization is performed through heating, the radically polymerizable raw material composition during the radical polymerization may be pressurized in order to suppress the formation of voids resulting from air bubbles in the cured body. A method for the pressurization is not limited, and mechanical pressurization may be performed, or pressurization with a gas such as nitrogen may be performed.

By performing the radical polymerization step as described above, there can be obtained a polyurethane-based composite material in which the filler (D) is dispersed in a polyurethane-based resin matrix.

Through appropriate control of radical polymerization conditions, the radical polymerization reaction may be carried out until unreacted radically polymerizable groups present in the radically polymerizable raw material composition are substantially completely consumed, or may be terminated under a state in which a certain amount of unreacted radically polymerizable groups remains in the cured body. For example, when a thermal polymerization initiator is utilized as the radical polymerization initiator (C), the degree of progress of the radical polymerization reaction (radically polymerizable group residual ratio) at the time of the termination of the radical polymerization reaction may be controlled by controlling the heating temperature and the heating time. However, in the method of producing a polyurethane-based composite material according to this embodiment, from the viewpoint of more reliably obtaining a cured body excellent in strength, the radically polymerizable group residual ratio is controlled so as not to become excessively large, and specifically, the radically polymerizable group residual ratio is particularly preferably controlled so as to fall within the range of from 0% to 25%. When the radically polymerizable group residual ratio is controlled to from 10% to 25%, a cured body excellent in strength, water resistance, and uniformity, and also excellent in bonding properties can be obtained. Meanwhile, in the case where the radically polymerizable group residual ratio is controlled to 0% or more and less than 10%, a cured body that is even more excellent in strength can be obtained, though the bonding properties are relatively reduced or lost, as compared to the case in which the radically polymerizable group residual ratio is controlled to from 10% to 25%.

In order to control the radically polymerizable group residual ratio to fall within the range of from 10% to 25%, it is suitable that the heating temperature and the heating time be set to fall within the following ranges (a1) and (b1).

(a1) Heating temperature: the range of from −10° C. to +25° C. with respect to the 10-hour half-life temperature of the thermal radical polymerization initiator to be used as the radical polymerization initiator (C)

(b1) Heating time: from 2 hours to 120 hours

In addition, from the viewpoints of controlling the radically polymerizable group residual ratio to fall within the range of from 10% to 25%, and more reliably preventing coloration and degeneration of the polyurethane-based composite material, the heating temperature and the heating time are set to fall within more suitably the following ranges (a2) and (b2), still more suitably the following ranges (a3) and (b3).

(a2) Heating temperature: the range of from +0° C. to +25° C. with respect to the 10-hour half-life temperature of the thermal radical polymerization initiator to be used as the radical polymerization initiator (C)

(b2) Heating time: from 5 hours to 72 hours (a3) Heating temperature: the range of from +10° C. to +25° C. with respect to the 10-hour half-life temperature of the thermal radical polymerization initiator to be used as the radical polymerization initiator (C)

(b3) Heating time: from 8 hours to 24 hours

Meanwhile, in order to control the radically polymerizable group residual ratio to fall within the range of less than 10%, it is suitable to select a relatively higher heating temperature and/or longer heating time as compared to the case in which the radically polymerizable group residual ratio is controlled to fall within the range of from 10% to 25%.

The above-mentioned “bonding properties” mean characteristics resulting from unreacted radically polymerizable groups that have not been involved in the radical polymerization, remaining in the polyurethane-based composite material, that is, improvements in bonding strength and bonding durability. The form of utilization of the polyurethane-based composite material in which such excellent bonding properties are exhibited is not particularly limited, but an example thereof is a case in which the polyurethane-based composite material having a radically polymerizable group residual ratio of from 10% to 25% and another material are bonded using an adhesive containing a radically polymerizable monomer.

The radically polymerizable group residual ratio may be calculated on the basis of peak areas at specific wavelengths obtained by subjecting the radically polymerizable raw material composition before the initiation of the radical polymerization and the cured body (polyurethane-based composite material) obtained after the termination of the radical polymerization of the radically polymerizable raw material composition to measurement by Fourier transform infrared spectroscopy (FT-IR). In this case, the radically polymerizable group residual ratio is calculated on the basis of the following equation (3).

$$\text{Radically polymerizable group residual ratio (\%)} = (r_1/r_0)\times 100 \qquad \text{Equation (3)}$$

In the equation (3), $r_0$ represents a normalized peak area ratio (ν6,170/ν4,920) obtained by normalizing a peak area (ν6,170) through division by a peak area (ν4,920) for two peak areas (ν6,170 and ν4,920) obtained through the FT-IR measurement of the radically polymerizable raw material composition before the initiation of the radical polymerization, and $r_1$ represents a normalized peak area ratio (ν6,170/ν4,920) obtained by normalizing a peak area (ν6,170) through division by a peak area (ν4,920) for two peak areas (ν6,170 and ν4,920) obtained through the FT-IR measurement of the cured body (polyurethane-based composite material) obtained after the termination of the radical polymerization.

Herein, the peak area (ν6,170) means the peak area of an absorption peak observed around 6, 170 $cm^{-1}$ attributable to the carbon-carbon double bond of a radically polymerizable group, and the peak area (ν4,920) means the peak area of an absorption peak observed around 4,920 $cm^{-1}$ attributable to the carbonyl group of a urethane bond.

4. Application Example of Method of Producing Polyurethane-Based Composite Material (Production of Material for Dental Cutting Work)

When the radically polymerizable raw material composition to be used in the method of producing a polyurethane-based composite material according to this embodiment is a paste-like composition, as described above, the radical polymerization step (curing step) can be carried out after the radically polymerizable raw material composition is poured into a mold. In addition, the cured body (polyurethane-based composite material) to be obtained also has water resistance while maintaining high strength even under a hydrophilic environment such as in the mouth. By virtue of achieving high water resistance as just described, the method of producing a polyurethane-based composite material according to this embodiment can be suitably used as a method of producing a material for dental cutting work particularly when a dental prosthesis is produced by subjecting the material for dental cutting work to cutting work through use of a dental CAD/CAM system. A suitable specific example of a case in which the method of producing a polyurethane-based composite material according to this embodiment is utilized for the production of the material for dental cutting work is described below.

First, a paste-like radically polymerizable raw material composition is prepared in the same manner as in the method of producing a polyurethane-based composite material according to this embodiment. Next, the radically polymerizable raw material composition is poured into a mold and then heated to carry out the radical polymerization step (curing step). The mold to be used for molding is not particularly limited, and a mold having a rectangular column shape, a cylindrical shape, a rectangular plate shape, or a disc shape is appropriately used in accordance with a shape assumed in advance for each product form. In addition, the dimensions and shape of the mold may be dimensions and a shape that are approximately equal to the dimensions and shape of the cured body after the radical polymerization in consideration of, for example, a shrinkage ratio at the time of the radical polymerization, or may be dimensions and a shape that are somewhat larger than the dimensions and shape of the obtained cured body on the assumption of a processing margin when the cured body obtained through the radical polymerization is processed in a subsequent step.

A method of pouring the paste-like radically polymerizable raw material composition into the mold is not particularly limited, and a known method may be used. However, pressure casting or vacuum casting is suitably adopted. When such pouring method is adopted, the entrapment of air bubbles into the cured body (polyurethane-based composite material) to be obtained and the formation of voids therein can be suppressed, and as a result, a material for dental cutting work excellent in strength and aesthetics can be obtained. In the case of pressure casting, a method for pressurization is not limited, and mechanical pressurization may be performed, or pressurization with a gas such as nitrogen may be performed.

After having been removed from the mold, the resultant cured body is subjected to post-treatment/post-processing, such as heat treatment for relaxing a residual stress, shape adjustment by cutting, and polishing, as required. Subsequently, to the cured body that has undergone such post-treatment/post-processing, a fixture such as a pin for holding the cured body onto a CAD/CAM device is further joined. Thus, the material for dental cutting work is obtained.

5. Polyurethane-Based Composite Material and Material for Dental Cutting Work

The polyurethane-based composite material produced by the method of producing a polyurethane-based composite material according to this embodiment is suitably produced by further satisfying production conditions described in (a) to (c) below in the method of producing a polyurethane-based composite material according to this embodiment. In this case, a cured body having a content of the filler (D) corresponding to the production condition described in (a) below and a radically polymerizable group residual ratio described in (d) below (polyurethane-based composite material according to a first embodiment of the present invention) can be obtained. The radically polymerizable group residual ratio described in (d) below is more suitably from 10% to 20%.

(a) The content ratio of the filler (D) in the radically polymerizable raw material composition is from 60 mass % to 85 mass %.

(b) A thermal radical polymerization initiator is used as the radical polymerization initiator (C).

(c) The radical polymerization step is carried out under heating at a temperature that is from −10° C. to +25° C. with respect to the 10-hour half-life temperature of the thermal radical polymerization initiator.

(d) 10% to 25% of the total amount of the radically polymerizable groups of the radically polymerizable diol compound (a1) and the non-polyadding radically polymerizable monomer (B) that are contained in the radically polymerizable raw material composition remains in a copolymer of the radically polymerizable polyurethane component (A) and the non-polyadding radically polymerizable monomer (B), the copolymer being formed in the radical polymerization step (i.e., its radically polymerizable group residual ratio is from 10% to 25%).

The polyurethane-based composite material according to the first embodiment of the present invention is a composite material produced by the method of producing a polyurethane-based composite material according to the above-mentioned embodiment, and hence is excellent in strength, water resistance, and uniformity, and moreover, also has excellent bonding properties by virtue of having a radically polymerizable group residual ratio of from 10% to 25%.

In addition, a polyurethane-based composite material according to a second embodiment of the present invention includes a composite material containing: a polyurethane-based resin matrix; and a filler dispersed and incorporated in the polyurethane-based resin matrix, wherein the polyurethane-based resin matrix is formed of a copolymer of: a polyurethane having a number average molecular weight of from 1,500 to 5,000 and having a radically polymerizable group; and a radically polymerizable monomer free from causing a polyaddition reaction with a hydroxyl group and an isocyanate group, wherein a content of radically polymerizable carbon-carbon double bonds per g of the polyurethane-based resin matrix is from 0.5 mmol/g to 1.0 mmol/g, and wherein a content of the filler in the composite material is from 60 mass % to 85 mass %. The "radically polymerizable monomer free from causing a polyaddition reaction with a hydroxyl group and an isocyanate group" means a compound having a molecular structure similar to the above-mentioned non-polyadding radically polymerizable monomer (B).

The polyurethane-based composite material according to the second embodiment of the present invention is the polyurethane-based composite material according to the first embodiment of the present invention identified from a different perspective in light of experimental data to be described later. Accordingly, the polyurethane-based composite material according to the second embodiment of the present invention, too, is not only excellent in strength, water resistance, and uniformity, but also has excellent bonding properties.

The content of radically polymerizable carbon-carbon double bonds per g of the polyurethane-based resin matrix (hereinafter sometimes referred to as "double bond amount") is preferably from 0.7 mmol/g to 1.0 mmol/g.

The double bond amount (mmol/g) in the polyurethane-based composite material according to the second embodiment of the present invention means a value determined by converting the value of the peak area (ν6,170), which has been obtained through FT-IR measurement of a measurement sample to be examined for its double bond amount, into the double bond amount through utilization of a calibration curve prepared in advance. However, when the measurement sample to be examined for its double bond amount is produced by the method of producing a polyurethane-based composite material according to the above-mentioned embodiment and its production conditions are known, as an exception, the double bond amount (mmol/g) in the polyurethane-based composite material according to the second embodiment of the present invention may be determined by using a theoretical double bond amount calculated on the basis of the following equation (4) to be described later as the double bond amount in the measurement sample.

In this case, the calibration curve is prepared by the following procedure. First, the method of producing a polyurethane-based composite material according to the above-mentioned embodiment is utilized to prepare a plurality of samples for calibration curve preparation produced under various production conditions. Here, for each of the samples for calibration curve preparation, a value for the radically polymerizable group residual ratio represented by the equation (3) is also determined by calculation. Next, for each of the samples for calibration curve preparation, a double bond amount in theory (theoretical double bond amount) is calculated on the basis of the following equation (4) to be described later. In addition, for each of the samples for calibration curve preparation, FT-IR measurement is carried out to measure the peak area (ν6, 170). Then, the values obtained for the respective samples for calibration curve preparation are plotted on a graph in which the X-axis represents the actually measured value of the peak area (ν6,170) obtained through the FT-IR measurement and the Y-axis represents the theoretical double bond amount (mmol/g). Thus, the calibration curve is obtained. FT-IR measurement conditions for the measurement sample and FT-IR measurement conditions for the samples for calibration curve preparation are set to be substantially identical to each other.

Theoretical double bond amount=initial double bond amount×radically polymerizable group residual ratio/100  Equation (4)

In the equation (4), the initial double bond amount means the total amount (mmol/g) of unreacted radically polymerizable groups in the raw material composition before the initiation of radical polymerization (the polyaddition-reactive raw material composition used for the preparation of the radically polymerizable raw material composition) at the time of the production of the sample for calibration curve preparation determined on the basis of the following equation (5), and the radically polymerizable group residual ratio means the radically polymerizable group residual ratio (%) determined on the basis of the equation (3).

Equation (5)

$$\text{Initial double bond amount} = \left\{\sum_{a=1}^{p}(Xa\times\alpha a)+\sum_{b=1}^{q}(Yb\times\beta b)\right\}/M$$

In the equation (5), "p" is an integer of 1 or more and represents the number of kinds of the radically polymerizable diol compounds (a1) contained in the polyaddition-reactive raw material composition used in the polyaddition reaction step, "a" represents an integer of from 1 to "p", "q" is an integer of 1 or more and represents the number of kinds of the non-polyadding radically polymerizable monomers (B) contained in the polyaddition-reactive raw material composition used in the polyaddition reaction step, and "b" represents an integer of from 1 to "q".

In addition, Xa represents the content (mmol) of an a-th radically polymerizable diol compound (a1) in the polyaddition-reactive raw material composition used in the polyaddition reaction step, aa represents the number of radically polymerizable groups contained per molecule of the a-th radically polymerizable diol compound (a1), Yb represents the content (mmol) of a b-th non-polyadding radically polymerizable monomer (B) in the polyaddition-reactive raw material composition used in the polyaddition reaction step, and Bb represents the number of radically polymerizable groups contained per molecule of the b-th non-polyadding radically polymerizable monomer (B).

Further, M represents the mass (g) of the polyaddition-reactive raw material composition used in the polyaddition reaction step. However, when the polyaddition-reactive raw material composition used in the polyaddition reaction step further contains an insoluble component (e.g., the filler (D)) that does not dissolve in any of the radically polymerizable diol compound (a1), the diisocyanate compound (a2), and the non-polyadding radically polymerizable monomer (B), M represents a mass (g) remaining after subtracting the mass (g) of the insoluble component contained in the polyaddition-reactive raw material composition from the mass (g) of the polyaddition-reactive raw material composition.

The polyurethane-based composite materials according to the first and second embodiments of the present invention are not only excellent in strength, water resistance, and uniformity, but also excellent in bonding properties as described above, and hence can be widely utilized in various applications. In particular, as a suitable application in which those four characteristics can be effectively put to good use, there is given, for example, a material for dental cutting work to be used in a dental CAD/CAM system. When dental prostheses are produced by the dental CAD/CAM system using materials for dental cutting work formed of the polyurethane-based composite materials according to the first and second embodiments of the present invention, the resultant dental prostheses are excellent in strength, water resistance, and aesthetics, and moreover, can also have satisfactory bonding properties and bonding durability with respect to dentin.

6. Polyurethane-Based Resin Materials

The polyurethane-based composite materials according to the first and second embodiments of the present invention each contain the filler (D) as an essential component, but may also be utilized in a mode in which the filler (D) is not included as an essential component. As suitable polyurethane-based resin materials based on this mode, there are given polyurethane-based resin materials according to first and second reference embodiments described below.

That is, it is preferred that the polyurethane-based resin material according to the first reference embodiment be produced through: a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), to thereby form a polyurethane component (A) having a number average molecular weight of from 1,500 to 5,000 and having a radically polymerizable group; a radically polymerizable raw material composition-preparing step of preparing a radically polymerizable raw material composition containing the polyurethane component (A), the polymerizable monomer (B), and a radical polymerization initiator (C); and a radical polymerization step of performing radical polymerization using the radically polymerizable raw material composition after completion of the polyaddition reaction step and the radically polymerizable raw material composition-preparing step, to thereby form a polyurethane-based resin material, wherein a polymerizable monomer blending ratio Rr represented by the following equation (1) is from 20 mass % to 80 mass %, wherein the radical polymerization initiator (C) to be used is a thermal radical polymerization initiator, wherein the radical polymerization step is carried out under heating at a temperature that is from −10° C. to +25° C. with respect to a 10-hour half-life temperature of the thermal radical polymerization initiator, and wherein 10% to 25% of a total amount of the radically polymerizable groups of the diol compound (a1) and the polymerizable monomer (B) that are contained in the radically polymerizable raw material composition remains in a copolymer of the polyurethane component (A) and the polymerizable monomer (B), the copolymer being formed in the radical polymerization step:

$$Rr=100\times Br/[a1r+a2r+Ar+Br] \quad \text{Equation (1)}$$

in the equation (1), a1r represents a content (parts by mass) of the diol compound (a1) remaining unreacted in the radically polymerizable raw material composition, a2r represents a content (parts by mass) of the diisocyanate compound (a2) remaining unreacted in the radically polymerizable raw material composition, Ar represents a content (parts by mass) of the polyurethane component (A) in the radically polymerizable raw material composition, and Br represents a content (parts by mass) of the polymerizable monomer (B) in the radically polymerizable raw material composition.

In addition, it is preferred that: the polyurethane-based resin material according to the second reference embodiment contain at least a copolymer of a polyurethane having a number average molecular weight of from 1,500 to 5,000 and having a radically polymerizable group, and a radically polymerizable monomer free from causing an addition reaction with a hydroxyl group and an isocyanate group; and the content of radically polymerizable carbon-carbon double bonds per g of a polyurethane-based resin matrix formed of the copolymer be from 0.5 mmol/g to 1.0 mmol/g.

The polyurethane-based resin materials according to the first and second reference embodiments may (i) contain 60 mass % to 85 mass % of the filler (D) like the polyurethane-based composite materials according to the first and second embodiments of the present invention as required, (ii) contain more than 0 mass % and less than 60 mass % or more than 85 mass % and less than 100 mass % of the filler (D), or (iii) be completely free of the filler (D). In addition, the polyurethane-based resin materials according to the first and second reference embodiments may contain one or more kinds of various additives, such as the filler (D), a fluorescent agent, an ultraviolet absorber, an antioxidant, a pigment, an antibacterial agent, and an X-ray contrast agent, as required.

EXAMPLES

Now, the present invention is described by way of Examples and Comparative Examples, but the present invention is by no means limited to these Examples.

1. Raw Materials

Components used in Examples and Comparative Examples and their abbreviations are shown below.

(1) Radically Polymerizable Diol Compound (a1)

GLM: glycerol monomethacrylate (OH-to-OH distance: 2)

bis-GMA: bisphenol A diglycidyl methacrylate (OH-to-OH distance: 19)

(2) Non-Radically Polymerizable Polyol Compound

PG: propylene glycol

GTP: glycerol tripropoxylate (average molecular weight=266)

(3) Diisocyanate Compound (a2)

XDI: m-xylylene diisocyanate (4) Non-Polyadding Radically Polymerizable Monomer (B)

1G: ethylene glycol dimethacrylate

2G: diethylene glycol dimethacrylate

3G: triethylene glycol dimethacrylate

9G: polyethylene glycol #400 dimethacrylate

A-TMPT-3EO: EO-modified trimethylolpropane triacrylate

A-DOG: dioxane glycol acrylate

UDMA: 1,6-bis(methacrylethyloxycarbonylamino)-2,2,4-trimethylhexane (5) Radical Polymerization Initiator (C)

PBL: t-butyl peroxylaurate (10-hour half-life temperature: 98° C.)

V-65: 2,2'-azobis(2,4-dimethylvaleronitrile) (10-hour half-life temperature: 51° C.)

BPO: benzoyl peroxide (10-hour half-life temperature: 74° C.)

(6) Filler (D)

F1: silica-zirconia (average particle diameter: 0.4 μm, 3-(trimethoxysilyl)propyl methacrylate surface treated product)

F2: silica-titania (average particle diameter: 0.08 μm, 3-(trimethoxysilyl)propyl methacrylate surface treated product)

2. Method of Producing Polyurethane-Based Composite Material

Examples of the method of producing a polyurethane-based composite material of the present invention are described below together with Comparative Examples.

Example A1

(1) Primary Raw Material Composition-Preparing Step

First, 10.63 parts by mass of GLM serving as a radically polymerizable diol compound (a1), 5.79 parts by mass of 1G serving as a non-polyadding radically polymerizable monomer (B), and 0.08 part by mass of PBL serving as a radical polymerization initiator (C) were mixed to prepare a mixed composition. Next, 49.70 parts by mass of F1 and 21.30 parts by mass of F2 serving as fillers (D) were added to the mixture composition, and the whole was kneaded. Thus, a primary raw material composition was prepared.

(2) Polyaddition Reaction Step and Radically Polymerizable Raw Material Composition-Preparing Step 12.50 Parts by mass of XDI serving as a diisocyanate compound (a2) was added into a rotation-revolution mixer containing the whole amount of the resultant primary raw material composition, and the contents were kneaded to prepare a polyaddition-reactive raw material composition. Next, the resultant polyaddition-reactive raw material composition was left to stand still in an incubator at 37° C. for 168 hours to perform a polyaddition reaction. Thus, a radically polymerizable polyurethane component (A) was formed, and a radically polymerizable raw material composition was prepared. The heating conditions (37° C./168 hours) at the time of the polyaddition reaction are conditions sufficient for the degree of progress of the polyaddition reaction to reach its maximum value (saturation value).

In this Example, the molar ratio of the diisocyanate compound (a2) to the radically polymerizable diol compound (a1) immediately after the preparation of the polyaddition-reactive raw material composition (hereinafter sometimes referred to as "a2/a1 molar ratio") is 1.0. In addition, the polymerizable monomer blending ratio Rr is 20 mass %. Further, the mass ratio (filling ratio) of the filler (D) in the mass of the radically polymerizable raw material composition is 71 mass %. In addition, except when heated to 37° C. in the polyaddition reaction, the various compositions were all prepared under an ordinary-temperature (25° C.) environment.

In this Example, the composition obtained by carrying out the polyaddition reaction step was used as it was as the radically polymerizable raw material composition. In addition, in this case, as described above, the following relationship is established: polymerizable monomer blending ratio Rp represented by the equation (1')=polymerizable monomer blending ratio Rr represented by equation (1). Accordingly, the polymerizable monomer blending ratio Rr shown in Table 1 was calculated using the equation (1').

(3) Evaluation of Radically Polymerizable Raw Material Composition (3-1) Number Average Molecular Weight Measurement (GPC Measurement) of Polyurethane Component (A)

1 g of the obtained radically polymerizable raw material composition was weighed in a screw-capped vial, and 3.5 ml of THF was added. The mixture was stirred, and the resultant THF solution was centrifuged with a centrifuge (manufactured by AS ONE Corporation) at 10,000 rpm for 10 minutes. Next, the supernatant obtained through the centrifugation was filtered through a membrane filter (PORE SIZE: 20 μm, manufactured by ADVANTEC TOYO KAISHA, LTD.) to provide a filtrate. Then, the filtrate was subjected to GPC measurement under GPC measurement conditions described below to determine the number average molecular weight in terms of polystyrene of the radically polymerizable polyurethane component (A) obtained through the polyaddition reaction. As a result, the number average molecular weight was found to be 3,500.

[GPC Measurement Conditions]

Measurement apparatus: Advanced Polymer Chromatography (manufactured by Nihon Waters K.K.)

Columns: ACQUITY APC™ XT 45, 1.7 μm
ACQUITY APC™ XT 125, 2.5 μm

Column temperature: 40° C.

Developing solvent: THF (flow rate: 0.5 ml/min)

Detector: photodiode array detector at 254 nm (PDA detector)

(3-2) Operability Evaluation

The operability of the radically polymerizable raw material composition was evaluated by measuring a maximum load at a time when a round bar made of stainless steel (SUS) having a diameter of 5 mm was pushed thereinto at a predetermined speed to a predetermined depth. The maximum load was measured by the following procedure. First, the radically polymerizable raw material composition was loaded into a nut-shaped mold made of SUS and its surface was leveled off, and the resultant was left to stand under a light-shielding condition for 2 minutes. Next, the nut-shaped mold made of SUS loaded with the radically polymerizable raw material composition, and a 5 mm bar made of SUS serving as a pressure-sensitive shaft were mounted onto Sun Rheometer CR-150 (manufactured by Sun Scientific Co., Ltd.). Subsequently, at 23° C., the pressure-sensitive shaft was compressed to enter the radically polymerizable raw material composition at a speed of 120 mm/min to a depth of 2 mm. In addition, the maximum load [Kg] at this time was measured. As a result, the maximum load was found to be 6.0 Kg.

When the maximum load is 10 Kg or less, the radically polymerizable raw material composition can be poured into a mold and molded. Accordingly, when the maximum load is 10 Kg or less, the operability is judged to be satisfactory, and when the maximum load is more than 10 Kg, the operability is judged to be unsatisfactory.

(3-3) Evaluation of Phase Form

The phase form of the radically polymerizable raw material composition was judged on the basis of the maximum load measured for the operability evaluation. In this case, when the maximum load was 10 Kg or less, the radically polymerizable raw material composition had fluidity sufficient for allowing the radically polymerizable raw material composition to be poured into a mold without a gap and easily molded, and hence the phase form of the radically polymerizable raw material composition was judged to be paste-like. Meanwhile, when the maximum load was more than 10 Kg, the radically polymerizable raw material composition lost fluidity so significantly that the radically polymerizable raw material composition was unable to be poured into a mold without a gap and molded, and hence the phase form of the radically polymerizable raw material composition was judged to be substantially solid. As a result, the obtained radically polymerizable raw material composition was recognized to be paste-like because its maximum load was 6.0 Kg.

(4) Radical Polymerization Step (Curing Step)

The obtained radically polymerizable raw material composition was poured into a mold (12 mm vertical×18 mm horizontal×14 mm thick), and subjected to radical polymerization at 120° C. for 15 hours under nitrogen pressure (0.35 MPa) to provide a polyurethane-based composite material in which the filler was dispersed in a polyurethane-based resin matrix. The obtained radically polymerizable raw material composition was not particularly observed to show an increase in viscosity or a change in liquidity during several hours from immediately after preparation to immediately before the initiation of molding and radical polymerization, and was thus recognized to be a composition stable under an ordinary-temperature environment. In addition, the cured body obtained by curing by the radical polymerization did not have a portion in which curing was partially insufficient, and hence a uniform cured body was obtained.

In addition, a radically polymerizable raw material composition separately prepared in the same manner was stored at ordinary temperature (25° C.) for 6 months and then evaluated for its phase form again, and as a result, was recognized as keeping its paste-like properties. In view of this, it was recognized that the obtained radically polymerizable raw material composition was capable of maintaining stable properties over an extremely long period of time. The same evaluation was also carried out for radically polymerizable raw material compositions used in other Examples shown in Tables 1 and 2, and it was recognized that the radically polymerizable raw material composition used in each of the Examples was also capable of maintaining stable properties over an extremely long period of time.

(5) Evaluation of Polyurethane-Based Composite Material (Cured Body)

The obtained polyurethane-based composite material was evaluated for its bending strength, underwater bending strength, maintenance ratio (water resistance), and uniformity. Evaluation methods and results are described below.

[Bending Strength $BS_d$]

The obtained polyurethane-based composite material (cured body) was cut with a low-speed diamond cutter (manufactured by Buehler Ltd.) and then polished using #2000 waterproof abrasive paper to produce ten test pieces each having a rectangular column shape (thickness: about 1.2 mm×width: about 4.0 mm×length: 14.0 mm). Next, each test piece was subjected to a three-point bending test using Autograph (manufactured by Shimadzu Corporation) to measure a bending load at a maximum point. Then, a bending strength BS was determined on the basis of the following equation (6). The bending load at the maximum point was measured with a support distance and a crosshead speed set to 12.0 mm and 1.0 mm/min, respectively. As a result, the average value (bending strength $BS_d$) of the bending strengths BS of the ten test pieces was found to be 337 MPa.

$$BS=3PS/2WB^2 \quad \text{Equation (6)}$$

In the equation (6), BS represents the bending strength (MPa), P represents the bending load (N) at the maximum point, S represents the support distance (12.0 mm), W represents the width of the test piece (actually measured value, mm), and B represents the thickness of the test piece (actually measured value, mm).

[Underwater Bending Strength $BS_W$]

Ten test pieces were produced in the same manner as in the case described in the [Bending Strength] section, and all the test pieces were stored in ion-exchanged water at 37° C. for 1 week. After that, water adhering to the surfaces of the test pieces removed from the ion-exchanged water was removed, and then the test pieces were subjected to a three-point bending test under the same test conditions as in the case described in the [Bending Strength] section to measure the bending load at the maximum point of each of the test pieces after storage in water. After that, for each of the test pieces after storage in water, the bending strength BS was determined on the basis of the equation (6). As a result, the average value (underwater bending strength $BS_w$) of the bending strengths BS of the ten test pieces after storage in water was found to be 283 MPa.

[Maintenance Ratio (Water Resistance)]

A maintenance ratio serving as an indicator of the water resistance of the cured body was calculated on the basis of the following equation (7). In this Example, the maintenance ratio was 84%, and thus it was recognized that the cured body had high water resistance.

$$\text{Maintenance ratio (\%)}=100\times BS_W/BS_d \quad \text{Equation (7)}$$

In the equation (7), $BS_W$ represents the average value (MPa) of the bending strengths BS of the ten test pieces after storage in water, and $BS_d$ represents the average value (MPa) of the bending strengths BS of the ten test pieces.

[Uniformity]

The external appearance of the obtained cured body and a cut surface obtained by cutting the cured body approximately in half were visually observed to evaluate the uniformity of the cured body. In this case, whether or not the cured body had uniformity was judged on the basis of whether or not curing unevenness was present in the surface and cut surface of the cured body and whether or not a crack was present therein; when neither curing unevenness nor a crack was found, the cured body was judged to be uniform, and when at least one of curing unevenness or a crack was found, the cured body was judged to be nonuniform. For the cured body of Example A1, neither curing unevenness nor a crack was found, and hence the cured body was found to be uniform.

Comparative Example A1

A primary raw material composition was prepared in the same manner as in Example A1. The diisocyanate compound (a2) [XDI] in the same amount as in Example A1 was added into a rotation-revolution mixer containing the whole amount of the resultant primary raw material composition, and the contents were kneaded to provide a raw material composition. This raw material composition is a composition having composition identical to the polyaddition-reactive raw material composition prepared in Example A1, and in the production process of a polyurethane-based composite material of Comparative Example A1, corresponds to a composition that serves both the functions of the polyaddition-reactive raw material composition and the radically polymerizable raw material composition that were used in Example A1.

Next, the resultant raw material composition was immediately poured into a mold (12 mm vertical×18 mm horizontal×14 mm thick), and a polyaddition reaction and radical polymerization were carried out simultaneously in parallel with each other at 120° C. for 15 hours under nitrogen pressure (0.35 MPa). Thus, a polyurethane-based composite material was obtained. The uniformity of the resultant polyurethane-based composite material (cured body) was examined, and as a result, it was recognized that the polyurethane-based composite material had a crack and was a nonuniform cured body. Accordingly, its bending strength, underwater bending strength, and maintenance ratio (water resistance) were not evaluated.

Examples A2 to A13

Radically polymerizable raw material compositions were prepared in the same manner as in Example A1 except that, in Example A1, the raw materials to be used, the a2/a1 molar ratio, the polymerizable monomer blending ratio Rr, and the filling ratio were changed as shown in Table 1. The resultant radically polymerizable raw material compositions were evaluated in the same manner as in Example A1. The results are shown in Table 2.

In addition, in the same manner as in Example A1, the resultant radically polymerizable raw material compositions were each poured into a mold, and then the radical polymerization step was carried out to produce polyurethane-based composite materials. The resultant polyurethane-based composite materials were evaluated in the same manner as in Example A1. The results are shown in Table 2.

(Comparative Examples A2 to A5) <Examples in which Non-Polyadding Radically Polymerizable Monomer (B) is not Incorporated, or Polymerizable Monomer Blending Ratio Rr Falls Outside Range of from 20 Mass % to 80 Mass %>

Radically polymerizable raw material compositions were prepared in the same manner as in Example A1 except that the raw materials to be used, the a2/a1 molar ratio, the polymerizable monomer blending ratio Rr, and the filling ratio were changed as shown in Table 1. The resultant radically polymerizable raw material compositions were evaluated in the same manner as in Example A1. The results are shown in Table 2.

In addition, in the same manner as in Example A1, the resultant radically polymerizable raw material compositions were each poured into a mold, and then the radical polymerization step was carried out to produce polyurethane-based composite materials. The resultant polyurethane-based composite materials were evaluated in the same manner as in Example A1. The results are shown in Table 2.

TABLE 1

| | Composition of radically polymerizable raw material composition*5 | | | | | | | | |
|---|---|---|---|---|---|---|---|---|---|
| | Matrix raw material composition | | | | | | | | |
| | | | | | B: Non-polyadding radically polymerizable monomer | | | | |
| | A: Radically polymerizable polyurethane component | | | | B: Non-polyadding | | | | Order of |
| No. | a1: Radically polymerizable diol compound (part(s) by mass) | a2 : Diisocyanate compound (part(s) by mass) | a2/a1 molar ratio | Number average molecular weight | radically polymerizable monomer (part(s) by mass) | Polymerizable monomer blending ratio Rr (mass %)*1 | C: Radical polymerization (part(s) by mass)*3 | D: Filler (filling ratio %)*2 | carrying out polyaddition reaction and radical polymerization |
| Example A1 | GLM (10.6) | XDI (12.5) | 1.00 | 3,500 | 1G (5.8) | 20 | PBL (0.08) | F1/F2 = 7/3 (71%) | Polyaddition reaction→radical polymerization |
| Example A2 | GLM (10.2) | XDI (12.1) | 1.01 | 3,000 | 1G (6.6) | 23 | PBL (0.08) | F1/F2 = 7/3 (71%) | Polyaddition reaction→radical polymerization |
| Example A3 | GLM (14.4) | XDI (16.6) | 1.00 | 3,500 | 1G (9.2) | 23 | PBL (0.11) | F1/F2 = 7/3 (60%) | Polyaddition reaction→radical polymerization |
| Example A4 | GLM (12.3) | XDI (14.6) | 1.01 | 3,300 | 1G (8.6) | 23 | PBL (0.10) | F1/F2 = 7/3 (65%) | Polyaddition reaction→radical polymerization |
| Example A5 | GLM (7.1) | XDI (8.3) | 1.00 | 2,000 | 1G (4.6) | 23 | PBL (0.06) | F1/F2 = 7/3 (80%) | Polyaddition reaction→radical polymerization |
| Example A6 | GLM (5.3) | XDI (6.2) | 0.99 | 1,800 | 1G (3.5) | 23 | PBL (0.04) | F1/F2 = 7/3 (85%) | Polyaddition reaction→radical polymerization |
| Example A7 | GLM (9.3) | XDI (11.0) | 1.01 | 2,700 | 2G (8.6) | 30 | PBL (0.11) | F1/F2 = 7/3 (71%) | Polyaddition reaction→radical polymerization |
| Example A8 | GLM (6.6) | XDI (7.8) | 1.00 | 2,500 | 1G (14.5) | 50 | PBL (0.10) | F1/F2 = 7/3 (71%) | Polyaddition reaction→radical polymerization |
| Example A9 | GLM (2.7) | XDI (3.1) | 0.99 | 1,500 | 1G (23.1) | 80 | PBL (0.15) | F1/F2 = 7/3 (71%) | Polyaddition reaction→radical polymerization |
| Example A10 | GLM (10.2) | XDI (12.1) | 1.01 | 2,700 | 3G | 23 | PBL (0.08) | F1/F2 = 7/3 (71%) | Polyaddition reaction→radical polymerization |

TABLE 1-continued

| | Composition of radically polymerizable raw material composition*[5] | | | | | | | | |
|---|---|---|---|---|---|---|---|---|---|
| | Matrix raw material composition | | | | | | | | |
| | A: Radically polymerizable polyurethane component | | | | B: Non-polyadding radically polymerizable monomer | | | | |
| No. | a1: Radically polymerizable diol compound (part(s) by mass) | a2 : Diisocyanate compound (part(s) by mass) | a2/a1 molar ratio | Number average molecular weight | B: Non-polyadding radically polymerizable monomer (part(s) by mass) | Polymerizable monomer blending ratio Rr (mass %)*[1] | C: Radical polymerization (part(s) by mass)*[3] | D: Filler (filling ratio %)*[2] | Order of carrying out polyaddition reaction and radical polymerization |
| Example A11 | GLM (10.2) | XDI (12.1) | 1.01 | 1,700 | 9G | 23 | PBL (0.08) | F1/F2 = 7/3 (71%) | Polyaddition reaction→radical polymerization |
| Example A12 | GLM (8.9) | XDI (10.5) | 1.01 | 2,900 | A-TMPT-3EO (9.5) | 33 | PBL (0.10) | F1/F2 = 7/3 (71%) | Polyaddition reaction→radical polymerization |
| Example A13 | GLM (8.9) | XDI (10.5) | 1.01 | 2,600 | A-DOG (9.5) | 33 | PBL (0.10) | F1/F2 = 7/3 (71%) | Polyaddition reaction→radical polymerization |
| Comparative Example A1 | GLM (10.6) | XDI (12.5) | 1.00 | — | 1G (5.8) | 20 | PBL (0.08) | F1/F2 = 7/3 (71%) | Polyaddition reaction and radical polymerization carried out simultaneously in parallel with each other |
| Comparative Example A2 | GLM (13.3) | XDI (15.7) | 1.00 | 4,000 | — | 0 | PBL (0.20) | F1/F2 = 7/3 (71%) | Polyaddition reaction→radical polymerization |
| Comparative Example A3 | GLM (11.9) | XDI (14.1) | 1.01 | 3,800 | 1G (2.9) | 10 | PBL (0.09) | F1/F2 = 7/3 (71%) | Polyaddition reaction→radical polymerization |
| Comparative Example A4 | GLM/bis-GMA = 13/7 (16.4) | XDI (12.5) | 0.86*[4] | 2,800 | — | 0 | PBL (0.08) | F1/F2 = 7/3 (71%) | Polyaddition reaction→radical polymerization |
| Comparative Example A5 | GLM (1.3) | XDI (1.6) | 1.00 | 1,000 | 1G (26.0) | 90 | PBL (0.08) | F1/F2 = 7/3 (71%) | Polyaddition reaction→radical polymerization |

*[1]Rr = 100 × Br/[a1r + a2r + Ar + Br]

*[2]The filling ratio means the mass ratio (mass %) of D: the filler in the mass of the radically polymerizable raw material composition. In addition, the F1/F2 ratio means a mass ratio.

*[3]The radical polymerization temperature in the curing step for obtaining the cured body is 120° C. (temperature higher than the 10-hour half-life temperature of C: the radical polymerization initiator by 22° C.) in all Examples and Comparative Examples.

*[4]XDI/GLM molar ratio = 1/1, GLM/bis-GMA molar ratio = 1/0.16.

*[5]The radically polymerizable raw material composition shown in Comparative Example A1 is a composition that also serves the function of the polyaddition-reactive raw material composition.

TABLE 2

| | Radically polymerizable raw material composition | | Polyurethane-based composite material (cured body) | | | |
|---|---|---|---|---|---|---|
| No. | Phase form | Operability (Kg) | Bending strength $BS_d$ (MPa) | Underwater bending strength $BS_w$ (MPa) | Maintenance ratio (%)*[1] | Uniformity |
| Example A1 | Paste-like | 6.0 | 337 | 283 | 84 | Uniform |
| Example A2 | Paste-like | 5.8 | 340 | 299 | 88 | Uniform |
| Example A3 | Paste-like | 4.2 | 325 | 270 | 83 | Uniform |
| Example A4 | Paste-like | 4.8 | 328 | 276 | 84 | Uniform |
| Example A5 | Paste-like | 6.3 | 330 | 274 | 83 | Uniform |
| Example A6 | Paste-like | 7.3 | 331 | 275 | 83 | Uniform |
| Example A7 | Paste-like | 5.6 | 320 | 275 | 86 | Uniform |
| Example A8 | Paste-like | 4.0 | 310 | 254 | 82 | Uniform |
| Example A9 | Paste-like | 2.8 | 300 | 243 | 81 | Uniform |
| Example A10 | Paste-like | 5.1 | 338 | 294 | 87 | Uniform |

TABLE 2-continued

| | Radically polymerizable raw material composition | | Polyurethane-based composite material (cured body) | | | |
|---|---|---|---|---|---|---|
| No. | Phase form | Operability (Kg) | Bending strength $BS_d$ (MPa) | Underwater bending strength $BS_w$ (MPa) | Maintenance ratio (%)*[1] | Uniformity |
| Example A11 | Paste-like | 4.3 | 300 | 252 | 84 | Uniform |
| Example A12 | Paste-like | 6.5 | 340 | 289 | 85 | Uniform |
| Example A13 | Paste-like | 8.7 | 319 | 278 | 87 | Uniform |
| Comparative Example A1 | Paste-like*[2] | — | — | — | — | Nonuniform (with crack) |
| Comparative Example A2 | Solid | >10.0 | 109 | 65 | 60 | Nonuniform (with curing unevenness) |
| Comparative Example A3 | Solid | >10.0 | 130 | 104 | 80 | Nonuniform (with curing unevenness) |
| Comparative Example A4 | Paste-like | 9.2 | 320 | 179 | 56 | Uniform |
| Comparative Example A5 | Paste-like | 2.0 | 290 | 235 | 81 | Uniform |

*[1]Maintenance ratio = 100 × $BS_w$ (MPa)/$BS_d$ (MPa)
*[2]Representing the phase form of the raw material composition.

As shown in Table 2, it was recognized that the polyurethane-based composite materials produced in Examples A1 to A13 were satisfactory in terms of all of strength (bending strength), water resistance, and uniformity. In addition, it was recognized that the operability of each of the radically polymerizable raw material compositions was also satisfactory, and besides, even when the filling ratio was as high as from 60% to 85%, curing progressed uniformly and sufficiently.

Meanwhile, in Comparative Example A1, in which the polyaddition reaction and the radical polymerization occurred simultaneously in parallel with each other, a uniform cured body was not obtained. In addition, in Comparative Example A2 not containing the non-polyadding radically polymerizable monomer (B), and Comparative Example A3 containing the non-polyadding radically polymerizable monomer (B) but having a polymerizable monomer blending ratio Rr of 20 mass % or less, the phase form was evaluated to be solid, a uniform cured body was not obtained, and the bending strength and the underwater bending strength had low values. In addition, in Comparative Example A4 not containing the non-polyadding radically polymerizable monomer (B) but using the radically polymerizable diol compound (a1) in an excess (with respect to the stoichiometric ratio), the phase form was evaluated to be paste-like, but the underwater bending strength had a low value. In addition, in Comparative Example A5 having the non-polyadding radically polymerizable monomer (B) blended so that the polymerizable monomer blending ratio Rr was more than 80 mass %, the underwater bending strength had a low value.

3. Polyurethane-Based Composite Material

Examples of a polyurethane-based composite material according to a first aspect of the present invention and a polyurethane-based composite material according to a second aspect of the present invention are described below together with Comparative Example.

Example B1

A cured body (polyurethane-based composite material) was produced by carrying out each step in the same manner as in Example A2. For the resultant cured body and the radically polymerizable raw material composition used for the production of the cured body, FT-IR measurement was performed to determine the radically polymerizable group residual ratio (%) represented by the equation (3). In addition, an initial double bond amount was calculated for the radically polymerizable raw material composition used for the production of the cured body on the basis of the equation (5), and then the double bond amount (mmol/g) of the cured body was determined on the basis of the equation (4). Further, the cured body was evaluated for its initial bonding strength, durable bonding strength, bending strength, underwater bending strength, and uniformity. The results are shown in Tables 3 and 4.

The FT-IR measurement of the cured body and the radically polymerizable raw material composition, and evaluation methods for the initial bonding strength and the durable bonding strength are as described below.

[FT-IR Measurement of Cured Body and Radically Polymerizable Raw Material Composition]

The FT-IR measurement of the obtained cured body and the radically polymerizable raw material composition used for the production of the cured body was performed by a transmission method using a Fourier transform infrared spectrophotometer (Spectrum One, manufactured by PerkinElmer, Inc.). The FT-IR measurement of the radically polymerizable raw material composition was carried out using as a measurement sample a sample obtained by loading the radically polymerizable raw material composition into a disc mold (15 mm in diameter×1 mm in thickness), and the FT-IR measurement of the cured body was carried out using as a measurement sample a sample obtained by curing the radically polymerizable raw material composition loaded in the disc mold under the same radical polymerization conditions as in the case of producing the cured body. In addition, for each of the measurement samples, two peak areas required for the calculation of the radically polymerizable group residual ratio (%) represented by the equation (3), that is, the peak area (ν4,920) of the absorption peak derived from the carbonyl group of a urethane bond and the peak area (ν6,170) of the absorption peak derived from the carbon-carbon double bond of a radically polymerizable group were measured.

[Initial Bonding Strength Evaluation]

The obtained cured body was cut with a low-speed diamond cutter (manufactured by Buehler Ltd.) and then polished using #1500 waterproof abrasive paper to provide a test piece (12 mm vertical×14 mm horizontal×3 mm thick). Next, the surface of the test piece was subjected to alumina sandblast treatment, ultrasonically cleaned with ion-exchanged water, and then dried by blowing dry air. Subsequently, a double-sided tape having a hole with a diameter of 3 mm was attached to the surface of the test piece, and a surface exposed through the hole was defined as a bonding surface. ESTECEM II (manufactured by Tokuyama Dental Corporation) was applied to the bonding surface, and then an attachment made of SUS having a cylindrical shape (diameter: 8 mm, length: 25 mm) was bonded to the bonding surface to provide a joined body. The resultant joined body was left to stand still under 37° C. and a wet condition for 1 hour and then immersed in water at 37° C. for 24 hours to provide a test piece with an attachment (measurement sample for initial bonding strength evaluation). A tensile test was performed using a universal tester (Autograph, manufactured by Shimadzu Corporation) at a crosshead speed of 2 mm/min. In this case, the average value of tensile bonding strengths measured for five measurement samples was defined as the initial bonding strength.

[Durable Bonding Strength Evaluation]

A test piece with an attachment produced in the same manner as in the case described in the [Initial Bonding Strength Evaluation] section was placed in a thermal shock tester, and then the following operation was repeated 3,000 times: the test piece was immersed in a water bath at 5° C. for 30 seconds, then transferred to a water bath at 55° C. and immersed therein for 30 seconds, and returned to the water bath at 5° C. again. Thus, a test piece with an attachment after a thermal shock test (measurement sample for durable bonding strength evaluation) was obtained. Next, its tensile bonding strength was measured in the same manner as in the case described in the [Initial Bonding Strength Evaluation] section. In this case, the average value of the tensile bonding strengths measured for five measurement samples was defined as the durable bonding strength.

Example B2

A cured body (polyurethane-based composite material) was produced by carrying out each step in the same manner as in Example A8. Then, in the same manner as in Example B1, the cured body was determined for its radically polymerizable group residual ratio (%) and double bond amount (mmol/g), and evaluated for its initial bonding strength and durable bonding strength. The results are shown in Tables 3 and 4.

Example B3

A cured body (polyurethane-based composite material) was produced by carrying out each step in the same manner as in Example A10. Then, in the same manner as in Example B1, the cured body was determined for its radically polymerizable group residual ratio (%) and double bond amount (mmol/g), and evaluated for its initial bonding strength and durable bonding strength. The results are shown in Tables 3 and 4.

Comparative Example B1

First, 19 parts by mass of UDMA, 6 parts by mass of 3G, and 0.1 part by mass of BPO were added together, and the mixture was stirred with a magnetic stirrer. Subsequently, 53 parts by mass of F1 and 22 parts by mass of F2 were added, and the whole was kneaded in a rotation-revolution mixer (manufactured by Kurabo Industries Ltd.) to provide a raw material composition. The resultant raw material composition was poured into a mold (12 mm vertical×18 mm horizontal×14 mm thick), and then, under nitrogen pressure (0.3 MPa), was increased in temperature to 90° C. and subjected to radical polymerization for 15 hours. After that, a cured body formed in the mold was removed from the mold. Then, in the same manner as in Example B1, the cured body was determined for its radically polymerizable group residual ratio (%) and double bond amount (mmol/g), and evaluated for its initial bonding strength and durable bonding strength. The results are shown in Tables 3 and 4.

TABLE 3

| | Production conditions for cured body | Number average molecular weight | Filling ratio (%) | Polymerizable monomer blending ratio Rr (mass %)*1 | Temperature difference at time of radical polymerization (° C.)*2 | Radically polymerizable group residual ratio (%) | Double bond amount (mmol/g) |
|---|---|---|---|---|---|---|---|
| Example B1 | Example A2 | 3,000 | 71 | 23 | +22 | 18 | 0.81 |
| Example B2 | Example A8 | 2,500 | 71 | 50 | +22 | 12 | 0.78 |
| Example B3 | Example A10 | 2,700 | 71 | 23 | +22 | 15 | 0.57 |
| Comparative Example B1 | *3 | — | 75 | 100 | +16 | 8 | 0.39 |

*1Rr = 100 × Br/[a1r + a2r + Ar + Br]

*210-hour half-life temperature of C: radical polymerization initiator (° C.)-heating temperature at time of radical polymerization (° C.)

*3: See description of Comparative Example B1 herein

TABLE 4

| | Initial bonding strength (MPa) | Durable bonding strength (MPa) | Bonding durability (%)*1 | Bending strength $BS_d$ (MPa) | Underwater bending strength $BS_w$ (MPa) | Maintenance ratio (%)*2 | Uniformity |
|---|---|---|---|---|---|---|---|
| Example B1 | 25.8 | 21.1 | 81.8 | See Example A2 in Table 2 | | | |
| Example B2 | 21.8 | 16.9 | 77.5 | See Example A8 in Table 2 | | | |

TABLE 4-continued

| | Initial bonding strength (MPa) | Durable bonding strength (MPa) | Bonding durability (%)*1 | Bending strength $BS_d$ (MPa) | Underwater bending strength $BS_w$ (MPa) | Maintenance ratio (%)*2 | Uniformity |
|---|---|---|---|---|---|---|---|
| Example B3 | 24.5 | 19.0 | 77.6 | See Example A10 in Table 2 | | | |
| Comparative Example B1 | 14.5 | 10.2 | 70.3 | 211 | 162 | 77 | Uniform |

*1 Bonding durability = 100 × durable bonding strength (MPa)/initial bonding strength (MPa)
*2 Maintenance ratio = 100 × $BS_w$ (MPa)/BSd (MPa)

As shown in Tables 3 and 4, it was recognized that, in Examples B1 to B3, both the initial bonding strength and the durable bonding strength were high as a result of the large double bond amount, and the ratio of the durable bonding strength to the initial bonding strength, i.e., the bonding durability was also as high as from 77.6% to 81.8%. Meanwhile, it was recognized that, in Comparative Example B1 having a small double bond amount, the initial bonding strength was as low as 14.5 MPa.

4. Polyurethane-Based Resin Matrix of Polyurethane-Based Composite Material

Experimental Examples of resin materials corresponding to polyurethane-based resin matrices forming the polyurethane-based composite material according to the first aspect of the present invention and the polyurethane-based composite material according to the second aspect of the present invention are described below.

In the following description, Experimental Examples A are Experimental Examples for resin materials corresponding to the polyurethane-based resin matrices forming the polyurethane-based composite material according to the first aspect of the present invention and the polyurethane-based composite material according to the second aspect of the present invention, and Experimental Examples B are Experimental Examples for resin materials not corresponding to the polyurethane-based resin matrices forming the polyurethane-based composite material according to the first aspect of the present invention and the polyurethane-based composite material according to the second aspect of the present invention.

Experimental Example A1

A cured body was produced in the same manner as in Example A2 except that the filler (D) was not blended in the preparation of the radically polymerizable raw material composition (see Table 5 for details of production conditions). Subsequently, in the same manner as in Example B1 corresponding to Example A2, the resultant cured body was determined for its radically polymerizable group residual ratio and double bond amount, and evaluated for its initial bonding strength and durable bonding strength. The results are shown in Table 6.

Experimental Example A2

A cured body was produced in the same manner as in Example A10 except that the filler (D) was not blended in the preparation of the radically polymerizable raw material composition (see Table 5 for details of production conditions). Subsequently, in the same manner as in Example B3 corresponding to Example A10, the resultant cured body was determined for its radically polymerizable group residual ratio and double bond amount, and evaluated for its initial bonding strength and durable bonding strength. The results are shown in Table 6.

Experimental Examples A3 to A7 and Experimental Examples B1 to B4

As apparent from comparative results between Examples B1 and B3 shown in Tables 3 and 4, and Experimental Examples A1 and A2 shown in Tables 5 and 6, it was recognized that whether or not the filler (D) was blended hardly influenced the double bond amount and the bonding durability. Accordingly, it is apparent that the difference of the polyurethane-based resin matrix is also directly reflected in the physical properties such as strength of a polyurethane-based composite material containing the polyurethane-based resin matrix and a filler dispersed and incorporated in the polyurethane-based resin matrix.

In view of the foregoing, in Experimental Examples A3 to A7 and Experimental Examples B1 to B3, resin materials corresponding to the polyurethane-based resin matrices were produced and subjected to various evaluations in the same manner as in Experimental Examples A1 and A2. The resin materials of Experimental Examples A3 to A7 and Experimental Examples B1 to B3 were produced under conditions shown in Table 5 on the basis of the method of producing a polyurethane-based composite material of the present invention except that the filler (D) was not used. In Experimental Examples A3 to A7 and Experimental Examples B1 to B4, the other production conditions not disclosed in Table 5 were the same as in Example A1.

In addition, in Experimental Example B4, a resin material produced by performing radical polymerization in the same manner as in Example A1 except that, as shown in Table 5, a radically polymerizable raw material composition containing only (meth)acrylic acid-based polymerizable monomers and a radical polymerization initiator was used as a starting raw material was subjected to various evaluations in the same manner as in Experimental Examples A1 and A2. The results are shown in Table 6.

TABLE 5

| | Composition of matrix raw material composition (radically polymerizable raw material composition containing no filler) | | | | | | | | | Radical polymerization conditions | |
|---|---|---|---|---|---|---|---|---|---|---|---|
| | A: Radically polymerizable polyurethane component and/or nA: non-radically polymerizable polyurethane component | | | | | | B: Non-polyadding radically polymerizable monomer | | | | |
| | a1: Radically polymerizable diol compound (part(s) by mass) | na1: Non-radically polymerizable polyol compound (part(s) by mass) | a2: Diisocyanate compound (part(s) by mass) | a2/a1 molar ratio | a2/na1 molar ratio | Number average molecular weight | B: Non-polyadding radically polymerizable monomer (part(s) by mass) | Polymerizable monomer blending ratio Rr (mass %)*[1] | C: Radical polymerization initiator (part(s) by mass) | Radical polymerization temperature (° C.) | Temperature difference at time of radical polymerization (° C.)*[2] |
| Experimental Example A1 | GLM (35) | — | XDI (41) | 1.0 | — | 3,000 | 1G (23) | 23 | PBL (0.5) | 120 | +22 |
| Experimental Example A2 | GLM (35) | — | XDI (41) | 1.0 | — | 2,800 | 3G (23) | 23 | PBL (0.5) | 120 | +22 |
| Experimental Example A3 | bis-GMA (49) | — | XDI (18) | 1.0 | — | 2,500 | 3G (33) | 33 | PBL (0.6) | 120 | +22 |
| Experimental Example A4 | GLM (35) | — | XDI (36) | 1.0 | — | 2,600 | 3G (33) | 33 | PBL (0.4) | 120 | +22 |
| Experimental Example A5 | GLM (18) | — | XDI (21) | 1.0 | — | 2,300 | 3G (60) | 60 | PBL (0.5) | 120 | +22 |
| Experimental Example A6 | GLM (35) | — | XDI (41) | 1.0 | — | 3,000 | 3G (23) | 23 | V-65 (05) | 90 | +29 |
| Experimental Example A7 | GLM (35) | — | XDI (41) | 1.0 | — | 3,000 | 3G (23) | 23 | PBL (0.5) | 90 | −8 |
| Experimental Example B1 | — | PG (19) | XDI (47) | — | 1.0 | 3,100 | 3G (33) | 41 | PBL (0.5) | 120 | +22 |
| Experimental Example B2 | — | GTP (24) | XDI (26) | — | 1.5*[3] | —*[4] | 3G (50) | 66 | PBL (0.5) | 120 | +22 |
| Experimental Example B3 | GLM (14) | PG (10) | XDI (42) | 2.5 | 1.7 | 3,200 | 3G (33) | 37 | PBL (0.5) | 120 | +22 |
| Experimental Example B4 | — | — | — | — | — | — | UDMA/3G = 3/1 (100) | 100 | BPO (0.5) | 90 | +16 |

*[1] $Rr = 100 \times Br/[a1r + a2r + Ar + Br]$

*[2] 10-hour half-life temperature of C: radical polymerization initiator (° C.)-heating temperature at time of radical polymerization (° C.)

*[3] GTP is a triol. Accordingly, the NCO/OH molar ratio is 1.0.

*[4] The molecular weight was unmeasurable due to crosslinking.

TABLE 6

| | Various characteristics of cured body | | | | |
|---|---|---|---|---|---|
| | Radically polymerizable group residual ratio (%) | Double bond amount (mmol/g) | Initial bonding strength (MPa) | Durable bonding strength (MPa) | Bonding durability (%)*[1] |
| Experimental Example A1 | 20 | 0.91 | 20.8 | 18.6 | 89.4 |
| Experimental Example A2 | 15 | 0.57 | 19.3 | 16.4 | 85.0 |
| Experimental Example A3 | 13 | 0.55 | 18.4 | 15.3 | 83.2 |
| Experimental Example A4 | 12 | 0.51 | 19.8 | 15.5 | 78.3 |
| Experimental Example A5 | 11 | 0.59 | 18.6 | 14.7 | 79.0 |
| Experimental Example A6 | 14 | 0.53 | 19.8 | 17.2 | 86.9 |
| Experimental Example A7 | 21 | 0.80 | 21.0 | 18.6 | 88.6 |
| Experimental Example B1 | 7 | 0.20 | 14.1 | 5.2 | 36.9 |
| Experimental Example B2 | 8 | 0.37 | 13.8 | 6.4 | 46.4 |
| Experimental Example B3 | 9 | 0.31 | 14.9 | 11.4 | 76.5 |
| Experimental Example B4 | 9 | 0.42 | 12.7 | 8.4 | 66.1 |

*[1] Bonding durability = 100 × durable bonding strength (MPa)/initial bonding strength (MPa)

As shown in Table 6, it was recognized that the radically polymerizable group residual ratios and double bond amounts of Experimental Examples A1 and A2 were respectively comparable or approximately comparable to the values in Examples B1 and B3. In addition, it was recognized that the absolute values of the initial bonding strength and the durable bonding strength tended to be slightly lower in Experimental Examples A1 and A2 owing to the incorporation of no filler than the values in Examples B1 and B3 (the values of the initial bonding strength ill and the durable bonding strength are lower by about 20% and about 12%, respectively), but satisfactory values were shown in all the cases, and moreover, the feature of having high bonding durability was maintained.

In addition, in each of Experimental Examples A1 to A7, the double bond amount falls within the range of from 0.51 mmol/g to 0.91 mmol/g, and both the initial bonding strength and the bonding durability show high values. In contrast, in Experimental Examples B1 and B2 each using a non-radically polymerizable diol compound in place of the radically polymerizable diol compound (a1), the double bond amount is as small as from 0.20 mmol/g to 0.37 mmol/g owing to the fewer radically polymerizable groups and the absence of copolymerization between the polyurethane component and the non-polyadding radically polymerizable monomer (B). As a result, in Experimental Examples B1 and B2, the initial bonding strength is from 13.8 MPa to 14.1 MPa, which is low as compared to Experimental Examples A1 to A7, and besides, the bonding durability is from 36.9% to 46.4%, which is extremely low as compared to Experimental Examples A1 to A7. In addition, in Experimental Example B3, in which the use ratio of the radically polymerizable diol compound (a1) to the diisocyanate compound (a2) is small, although the double bond amount is as small as 0.31 mmol/g and the bonding durability is 76.5%, the initial bonding strength has a low value of 14.9 MPa. In addition, in Experimental Example B4, in which the obtained resin material is (meth)acrylic acid-based, the initial bonding strength has a low value of 12.7 MPa.

The invention claimed is:

1. A method of producing a polyurethane-based composite material, comprising:

a polyaddition reaction step of subjecting a diol compound (a1) having one or more radically polymerizable groups and a diisocyanate compound (a2) to a polyaddition reaction in a polyaddition-reactive raw material composition containing the diol compound (a1), the diisocyanate compound (a2), and a polymerizable monomer (B) having one or more radically polymerizable groups in a molecule, and being free from causing a polyaddition reaction with any of the diol compound (a1) and the diisocyanate compound (a2), and free of a catalyst for accelerating the polyaddition reaction, at a temperature of 30° C. to 100° C., to thereby form a polyurethane component (A) having a number average molecular weight of from 1,500 to 5,000 and having a radically polymerizable group in side chains;

a radically polymerizable raw material composition-preparing step of preparing a paste-like radically polymerizable raw material composition containing the polyurethane component (A), the polymerizable monomer (B), a radical polymerization initiator (C), and a filler (D); and a radical polymerization step of performing radical polymerization using the paste-like radically polymerizable raw material composition after completion of the polyaddition reaction step and the radically polymerizable raw material composition-preparing step, to thereby form a polyurethane-based composite material, wherein a content ratio of the filler (D) in the paste-like radically polymerizable raw material composition is from 71 mass % to 85 mass %, a polymerizable monomer blending ratio Rr represented by the following equation (1) is from 20 mass % to 80 mass %:

$$Rr=100\times Br/[a1r+a2r+Ar+Br], \text{ and} \qquad \text{Equation (1)}$$

in the equation (1), a1r represents a content (parts by mass) of the diol compound (a1) remaining unreacted in the paste-like radically polymerizable raw material composition, a2r represents a content (parts by mass) of the diisocyanate compound (a2) remaining unreacted in the paste-like radically polymerizable raw material composition, Ar represents a content (parts by mass) of the polyurethane component (A) in the paste-like radically polymerizable raw material composition, and Br represents a content (parts by mass) of the polymerizable monomer (B) in the paste-like radically polymerizable raw material composition.

2. The method of producing a polyurethane-based composite material according to claim 1, wherein the polymerizable monomer (B) contains a polymerizable monomer represented by the following structural formula (1):

(1)

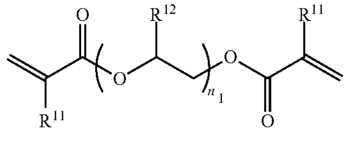

in the structural formula (1), $R^{11}$ and $R^{12}$ each represent a hydrogen atom or a methyl group, and $n_1$ represents an integer of from 1 to 10.

3. The method of producing a polyurethane-based composite material according to claim 1, wherein the diol compound (a1) is a diol compound in which a number of constituent atoms of a main chain in a divalent organic residue interposed between two hydroxyl groups contained in the diol compound is from 2 to 8.

4. The method of producing a polyurethane-based composite material according to claim 1, wherein the radical polymerization initiator (C) to be used is a thermal radical polymerization initiator, and wherein the radical polymerization step is carried out under heating at a temperature that is from −10° C. to +25° C. with respect to a 10-hour half-life temperature of the thermal radical polymerization initiator.

5. The method of producing a polyurethane-based composite material according to claim 1, wherein the polyaddition-reactive raw material composition is prepared by:

preparing a primary raw material composition containing the diol compound (a1), the polymerizable monomer (B), and the filler (D); and further adding the diisocyanate compound (a2) to the primary raw material composition.

6. The method of producing a polyurethane-based composite material according to claim 1, wherein the radical polymerization step is carried out after the paste-like radically polymerizable raw material composition is poured into a mold.

* * * * *